(12) United States Patent
Leichner et al.

(10) Patent No.: US 12,661,219 B2
(45) Date of Patent: Jun. 23, 2026

(54) SOUND AND VIBRATION SENSORS FOR ESTIMATING PROSTHETIC VALVE DIAMETER DURING EXPANSION

(71) Applicant: EDWARDS LIFESCIENCES CORPORATION, Irvine, CA (US)

(72) Inventors: Joseph Mordechai Leichner, Netanya (IL); Anatoly Dvorsky, Haifa (IL); Michal Aliza Ruchelsman, Zichron-Yaakov (IL)

(73) Assignee: Edwards Lifesciences Corporation, Irvine, CA (US)

( * ) Notice: Subject to any disclaimer, the term of this patent is extended or adjusted under 35 U.S.C. 154(b) by 625 days.

(21) Appl. No.: 18/136,944

(22) Filed: Apr. 20, 2023

(65) Prior Publication Data

US 2023/0255752 A1     Aug. 17, 2023

Related U.S. Application Data

(63) Continuation of application No. PCT/US2021/055563, filed on Oct. 19, 2021.

(60) Provisional application No. 63/094,099, filed on Oct. 20, 2020.

(51) Int. Cl.
*A61F 2/24* (2006.01)
*A61F 2/95* (2013.01)

(52) U.S. Cl.
CPC .............. *A61F 2/24* (2013.01); *A61F 2/9517* (2020.05); *A61F 2220/0025* (2013.01)

(58) Field of Classification Search
CPC .. A61F 2/2418; A61F 2/95; A61F 2/24; A61F 2220/0025; A61F 2/2433; A61F 2/2427;
A61F 2002/9583; A61F 2/2466; A61F 2/2409; A61F 2220/0008; A61F 2/2463; A61F 2/2454; A61F 2240/00; A61F 2/246; A61F 2/2439; A61F 2/82; A61F 2/07; A61F 2/93; A61F 2/94; A61F 2/86; A61F 2/9522
See application file for complete search history.

(56) References Cited

U.S. PATENT DOCUMENTS

| | | | |
|---|---|---|---|
| 519,297 | A | 5/1894 | Wanek et al. |
| 4,035,849 | A | 7/1977 | Angell et al. |
| 4,592,340 | A | 6/1986 | Boyles |
| 4,955,895 | A | 9/1990 | Sugiyama et al. |
| 4,994,077 | A | 2/1991 | Dobben |
| 5,059,177 | A | 10/1991 | Towne et al. |
| 5,176,698 | A | 1/1993 | Burns et al. |
| 5,192,297 | A | 3/1993 | Hull |
| 5,266,073 | A | 11/1993 | Wall |
| 5,325,845 | A | 7/1994 | Adair |
| 5,358,496 | A | 10/1994 | Ortiz et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Seema Mathew
(74) *Attorney, Agent, or Firm* — Webb & Co.

(57) ABSTRACT

The present invention relates to systems, assemblies and methods for estimating prosthetic valve expansion diameter, and in particular, for system and assemblies equipped with at least one sound or vibration sensor configured to provide real-time estimate of prosthetic valve expansion diameter.

20 Claims, 12 Drawing Sheets

(56)                References Cited

U.S. PATENT DOCUMENTS

| | | | |
|---|---|---|---|
| 5,411,552 A | | 5/1995 | Andersen et al. |
| 5,480,423 A | * | 1/1996 | Ravenscroft ............. A61F 2/95 |
| | | | 623/1.11 |
| 5,554,185 A | | 9/1996 | Block et al. |
| 5,591,195 A | | 1/1997 | Taheri et al. |
| 5,599,305 A | | 2/1997 | Hermann et al. |
| 5,632,760 A | | 5/1997 | Sheiban et al. |
| 5,639,274 A | | 6/1997 | Fischell et al. |
| 5,728,068 A | | 3/1998 | Leone et al. |
| 5,749,890 A | | 5/1998 | Shaknovich |
| 5,782,809 A | | 7/1998 | Umeno et al. |
| 5,824,044 A | | 10/1998 | Quiachon et al. |
| 5,840,081 A | | 11/1998 | Andersen et al. |
| 5,908,405 A | | 6/1999 | Imran et al. |
| 5,916,147 A | | 6/1999 | Boury |
| 5,944,690 A | | 8/1999 | Falwell et al. |
| 5,961,536 A | | 10/1999 | Mickley et al. |
| 5,968,068 A | | 10/1999 | Dehdashtian et al. |
| 6,019,777 A | | 2/2000 | Mackenzie |
| 6,027,510 A | | 2/2000 | Alt |
| 6,033,381 A | | 3/2000 | Kontos |
| 6,143,016 A | | 11/2000 | Bleam et al. |
| 6,162,208 A | | 12/2000 | Hipps |
| 6,168,614 B1 | | 1/2001 | Andersen et al. |
| 6,174,327 B1 | | 1/2001 | Mertens et al. |
| 6,217,585 B1 | | 4/2001 | Houser et al. |
| 6,235,050 B1 | | 5/2001 | Quiachon et al. |
| 6,251,092 B1 | | 6/2001 | Qin et al. |
| 6,379,372 B1 | | 4/2002 | Dehdashtian et al. |
| 6,383,171 B1 | | 5/2002 | Gifford et al. |
| 6,454,799 B1 | | 9/2002 | Schreck |
| 6,458,153 B1 | | 10/2002 | Bailey et al. |
| 6,461,382 B1 | | 10/2002 | Cao |
| 6,471,672 B1 | | 10/2002 | Brown et al. |
| 6,500,147 B2 | | 12/2002 | Omaleki et al. |
| 6,514,228 B1 | | 2/2003 | Hamilton et al. |
| 6,527,979 B2 | | 3/2003 | Constantz et al. |
| 6,579,305 B1 | | 6/2003 | Lashinski |
| 6,582,462 B1 | | 6/2003 | Andersen et al. |
| 6,652,578 B2 | | 11/2003 | Bailey et al. |
| 6,730,118 B2 | | 5/2004 | Spenser et al. |
| 6,733,525 B2 | | 5/2004 | Yang et al. |
| 6,764,504 B2 | | 7/2004 | Wang et al. |
| 6,767,362 B2 | | 7/2004 | Schreck |
| 6,830,584 B1 | | 12/2004 | Seguin |
| 6,893,460 B2 | | 5/2005 | Spenser et al. |
| 6,908,481 B2 | | 6/2005 | Cribier |
| 7,011,094 B2 | | 3/2006 | Rapacki et al. |
| 7,018,406 B2 | | 3/2006 | Seguin et al. |
| 7,018,408 B2 | | 3/2006 | Bailey et al. |
| 7,137,993 B2 | | 11/2006 | Acosta et al. |
| 7,276,084 B2 | | 10/2007 | Yang et al. |
| 7,318,278 B2 | | 1/2008 | Zhang et al. |
| 7,320,702 B2 | | 1/2008 | Hammersmark et al. |
| 7,320,704 B2 | | 1/2008 | Lashinski et al. |
| 7,374,571 B2 | | 5/2008 | Pease et al. |
| 7,393,360 B2 | | 7/2008 | Spenser et al. |
| 7,435,257 B2 | | 10/2008 | Lashinski et al. |
| 7,510,575 B2 | | 3/2009 | Spenser et al. |
| 7,585,321 B2 | | 9/2009 | Cribier |
| 7,594,926 B2 | | 9/2009 | Linder et al. |
| 7,597,709 B2 | | 10/2009 | Goodin |
| 7,618,446 B2 | | 11/2009 | Andersen et al. |
| 7,780,723 B2 | | 8/2010 | Taylor |
| 7,785,366 B2 | | 8/2010 | Maurer et al. |
| 7,959,661 B2 | | 6/2011 | Hijlkema et al. |
| 7,959,666 B2 | * | 6/2011 | Salahieh ................ A61F 2/243 |
| | | | 623/1.26 |
| 8,029,556 B2 | | 10/2011 | Rowe |
| 8,167,932 B2 | | 5/2012 | Bourang et al. |
| 8,449,606 B2 | | 5/2013 | Eliasen et al. |
| 8,475,523 B2 | | 7/2013 | Duffy |
| 8,568,472 B2 | | 10/2013 | Marchand et al. |
| 9,061,119 B2 | | 6/2015 | Le et al. |
| 9,119,716 B2 | | 9/2015 | Lee et al. |
| 9,795,477 B2 | | 10/2017 | Tran et al. |
| 11,273,038 B2 | | 3/2022 | Tang et al. |
| 2001/0002445 A1 | | 5/2001 | Vesely |
| 2001/0007082 A1 | | 7/2001 | Dusbabek et al. |
| 2002/0032481 A1 | | 3/2002 | Gabbay |
| 2002/0058995 A1 | | 5/2002 | Stevens |
| 2002/0165461 A1 | | 11/2002 | Hayzelden et al. |
| 2003/0040792 A1 | | 2/2003 | Gabbay |
| 2003/0050694 A1 | | 3/2003 | Yang et al. |
| 2003/0120341 A1 | | 6/2003 | Shennib et al. |
| 2004/0093061 A1 | | 5/2004 | Acosta et al. |
| 2004/0133263 A1 | | 7/2004 | Dusbabek et al. |
| 2004/0143197 A1 | | 7/2004 | Soukup et al. |
| 2004/0186563 A1 | | 9/2004 | Lobbi |
| 2004/0186565 A1 | | 9/2004 | Schreck |
| 2004/0260389 A1 | | 12/2004 | Case et al. |
| 2005/0080474 A1 | * | 4/2005 | Andreas .................. A61F 2/958 |
| | | | 623/1.11 |
| 2005/0096736 A1 | | 5/2005 | Osse et al. |
| 2005/0137689 A1 | | 6/2005 | Salahieh et al. |
| 2005/0149159 A1 | * | 7/2005 | Andreas ............ A61M 25/0136 |
| | | | 623/1.11 |
| 2005/0149160 A1 | * | 7/2005 | McFerran ................ A61F 2/95 |
| | | | 623/1.11 |
| 2005/0203614 A1 | | 9/2005 | Forster et al. |
| 2005/0203617 A1 | | 9/2005 | Forster et al. |
| 2005/0245894 A1 | | 11/2005 | Zadno Azizi |
| 2006/0025857 A1 | | 2/2006 | Bergheim et al. |
| 2006/0241748 A1 | * | 10/2006 | Lee ...................... A61F 2/2445 |
| | | | 623/2.37 |
| 2006/0282150 A1 | * | 12/2006 | Olson .............. A61M 25/0136 |
| | | | 623/1.11 |
| 2007/0005131 A1 | | 1/2007 | Taylor |
| 2007/0073389 A1 | | 3/2007 | Bolduc et al. |
| 2007/0088431 A1 | | 4/2007 | Bourang et al. |
| 2007/0100356 A1 | | 5/2007 | Lucatero et al. |
| 2007/0112422 A1 | | 5/2007 | Dehdashtian |
| 2007/0203575 A1 | | 8/2007 | Forster et al. |
| 2007/0219612 A1 | | 9/2007 | Andreas et al. |
| 2007/0239254 A1 | | 10/2007 | Chia et al. |
| 2007/0244546 A1 | | 10/2007 | Francis |
| 2007/0265700 A1 | | 11/2007 | Eliasen et al. |
| 2008/0065011 A1 | | 3/2008 | Marchand et al. |
| 2008/0103520 A1 | | 5/2008 | Selkee |
| 2008/0125853 A1 | | 5/2008 | Bailey et al. |
| 2008/0294230 A1 | | 11/2008 | Parker |
| 2009/0024428 A1 | | 1/2009 | Hudock |
| 2009/0069889 A1 | | 3/2009 | Suri et al. |
| 2009/0138079 A1 | | 5/2009 | Tuval et al. |
| 2009/0149872 A1 | * | 6/2009 | Gross .................... A61F 2/2457 |
| | | | 606/139 |
| 2009/0157175 A1 | | 6/2009 | Benichou |
| 2009/0192585 A1 | | 7/2009 | Bloom et al. |
| 2009/0228093 A1 | | 9/2009 | Taylor et al. |
| 2009/0276040 A1 | | 11/2009 | Rowe et al. |
| 2009/0281619 A1 | | 11/2009 | Le et al. |
| 2009/0299456 A1 | | 12/2009 | Melsheimer |
| 2009/0319037 A1 | | 12/2009 | Rowe et al. |
| 2010/0030318 A1 | | 2/2010 | Berra |
| 2010/0036472 A1 | | 2/2010 | Papp |
| 2010/0036473 A1 | | 2/2010 | Roth |
| 2010/0049313 A1 | * | 2/2010 | Alon .................... A61F 2/2418 |
| | | | 623/2.11 |
| 2010/0076402 A1 | | 3/2010 | Mazzone et al. |
| 2010/0076541 A1 | | 3/2010 | Kumoyama |
| 2010/0082089 A1 | | 4/2010 | Quadri et al. |
| 2010/0094394 A1 | | 4/2010 | Beach et al. |
| 2010/0121425 A1 | | 5/2010 | Shimada |
| 2010/0145431 A1 | * | 6/2010 | Wu ........................ A61F 2/966 |
| | | | 623/1.11 |
| 2010/0161036 A1 | | 6/2010 | Pintor et al. |
| 2010/0174363 A1 | | 7/2010 | Castro |
| 2010/0198347 A1 | | 8/2010 | Zakay et al. |
| 2010/0274344 A1 | | 10/2010 | Dusbabek et al. |
| 2011/0015729 A1 | | 1/2011 | Jimenez et al. |
| 2011/0054596 A1 | | 3/2011 | Taylor |
| 2011/0137331 A1 | | 6/2011 | Walsh et al. |
| 2011/0160846 A1 | | 6/2011 | Bishop et al. |

(56)                  References Cited

U.S. PATENT DOCUMENTS

| | | | |
|---|---|---|---|
| 2012/0123529 A1 | 5/2012 | Levi et al. | |
| 2012/0239142 A1 | 9/2012 | Liu et al. | |
| 2013/0030519 A1 | 1/2013 | Tran et al. | |
| 2013/0166017 A1* | 6/2013 | Cartledge | A61F 2/2439 |
| | | | 623/1.2 |
| 2013/0317598 A1 | 11/2013 | Rowe et al. | |
| 2014/0296962 A1 | 10/2014 | Cartledge et al. | |
| 2016/0256274 A1* | 9/2016 | Hayoz | A61F 2/2448 |
| 2017/0065415 A1 | 3/2017 | Rupp et al. | |
| 2018/0153689 A1 | 6/2018 | Maimon et al. | |
| 2018/0344456 A1 | 12/2018 | Barash et al. | |
| 2019/0328501 A1* | 10/2019 | Sun | A61F 5/00 |
| 2023/0007515 A1* | 1/2023 | Xu | H04W 72/23 |
| 2023/0255752 A1* | 8/2023 | Leichner | A61F 2/2418 |
| | | | 623/2.1 |
| 2025/0134659 A1* | 5/2025 | Dehdashtian | A61F 2/2436 |
| 2025/0205048 A1* | 6/2025 | Morrissey | A61F 2/2412 |
| 2025/0312154 A1* | 10/2025 | Zeng | A61F 2/2436 |

FOREIGN PATENT DOCUMENTS

| | | | | |
|---|---|---|---|---|
| EP | 0592410 | B1 | 10/1995 | |
| EP | 0850607 | A1 | 7/1998 | |
| FR | 2815844 | A1 | 5/2002 | |
| JP | 2007516044 | A * | 6/2007 | A61F 2/95 |
| WO | 1991017720 | A1 | 11/1991 | |
| WO | 1998029057 | A1 | 7/1998 | |
| WO | 1999012483 | A1 | 3/1999 | |
| WO | 2001049213 | A2 | 7/2001 | |
| WO | 2001054625 | A1 | 8/2001 | |
| WO | 2001076510 | A2 | 10/2001 | |
| WO | 2002022054 | A1 | 3/2002 | |
| WO | 2002036048 | A1 | 5/2002 | |
| WO | 2002047575 | A2 | 6/2002 | |
| WO | 2002060352 | A1 | 8/2002 | |
| WO | 2003030776 | A2 | 4/2003 | |
| WO | 2003047468 | A1 | 6/2003 | |
| WO | 2004019825 | A1 | 3/2004 | |
| WO | 2005084595 | A1 | 9/2005 | |
| WO | 2005102015 | A2 | 11/2005 | |
| WO | 2006032051 | A2 | 3/2006 | |
| WO | 2006111391 | A1 | 10/2006 | |
| WO | 2006138173 | A2 | 12/2006 | |
| WO | 2007047488 | A2 | 4/2007 | |
| WO | 2007067942 | A1 | 6/2007 | |
| WO | 2010121076 | A2 | 10/2010 | |
| WO | WO-2014081796 | A1 * | 5/2014 | A61F 2/2412 |
| WO | WO-2021167983 | A1 * | 8/2021 | A61B 5/026 |
| WO | WO-2023137024 | A1 * | 7/2023 | A61F 2/2436 |
| WO | WO-2025188826 | A1 * | 9/2025 | A61B 17/3478 |

* cited by examiner

SOUND AND VIBRATION SENSORS FOR ESTIMATING PROSTHETIC VALVE DIAMETER DURING EXPANSION

CROSS REFERENCE TO RELATED APPLICATIONS

This application is a continuation of International Application No. PCT/US2021/055563, filed Oct. 19, 2021, which claims benefit of U.S. Provisional Application No. 63/094,099, filed on Oct. 20, 2020, the contents of each of which are herein incorporated by reference in their entirety.

FIELD OF THE INVENTION

The present invention relates to systems, assemblies and methods for estimating prosthetic valve expansion diameter, and in particular, for system and assemblies equipped with at least one sound or vibration sensor configured to provide real-time estimate of prosthetic valve expansion diameter.

BACKGROUND OF THE INVENTION

Native heart valves, such as the aortic, pulmonary and mitral valves, function to assure adequate directional flow from and to the heart, and between the heart's chambers, to supply blood to the whole cardiovascular system. Various valvular diseases can render the valves ineffective and require replacement with artificial valves. Surgical procedures can be performed to repair or replace a heart valve. Surgeries are prone to an abundance of clinical complications, hence alternative less invasive techniques of delivering a prosthetic heart valve over a catheter and implanting it over the native malfunctioning valve, have been developed over the years.

Mechanically expandable valves are a category of prosthetic valves that rely on a mechanical actuation mechanism for expansion. The actuation mechanism usually includes a plurality of actuation/locking assemblies, releasably connected to respective actuation members of the valve delivery system, controlled via the handle for actuating the assemblies to expand the valve to a desired diameter. The assemblies may optionally lock the valve's position to prevent undesired recompression thereof, and disconnection of the delivery system's actuation member from the valve actuation/locking assemblies, to enable retrieval thereof once the valve is properly positioned at the desired site of implantation.

When implanting a prosthetic valve, such as a mechanically expandable valve, it is desirable to expand the valve to a maximum size allowed by the patient's anatomical considerations, in order to avoid paravalvular leakage or other unfavorable hemodynamic phenomena across the valve that may be associated with a mismatch between the valve's expansion diameter and the surrounding tissue, while mitigating the risk of annular rupture that may result from over-expansion. To ensure optimal implantation size, the diameter of the prosthetic valve should be monitored in real-time during the implantation procedure.

SUMMARY OF THE INVENTION

The present disclosure is directed toward devices, assemblies and methods for monitoring radial expansion of a prosthetic valve during prosthetic valve implantation procedures. Real-time measurement of the expansion diameter ensures proper implantation of the prosthetic valve within a designated site of implantation, such as the site of malfunctioning native valve.

According to one aspect of the invention, there is provided a prosthetic valve expansion monitoring system comprising a prosthetic valve, a delivery apparatus and at least one sound sensor. The prosthetic valve comprises a frame movable between a radially compressed configuration and a radially expanded configuration, and at least one expansion and locking assembly. The at least one expansion and locking assembly comprises an outer member coupled to the frame at a first location, and an inner member, coupled to the frame at a second location spaced apart from the first location. The inner member extends at least partially into the outer member, and comprises a plurality of ratcheting teeth.

The delivery apparatus comprises a handle, a delivery shaft extending distally from the handle, and at least one actuation assembly. The at least one actuation assembly comprises an actuator extending from the handle through the delivery shaft, and a sleeve disposed around the corresponding actuator. The actuator is releasably coupled to the corresponding inner member.

The spring biased arm is biased toward the inner member, wherein engagement of the pawl with the ratcheting teeth allows movement in a first direction to allow axial foreshortening and radial expansion of the frame and prevents movement in a second direction to prevent radial compression of the frame.

The sound sensor is configured to generate signals commensurate with click sounds generated during movement of the pawl over the ratcheting teeth.

In some examples, the system further comprises a control unit configured to: receive the signals from the at least one sound sensor; responsive to the received signals, determine the number of click sounds generated during the movement of the pawl; evaluate an expanded diameter of the prosthetic valve; and output an indication of the evaluated expanded diameter.

In some examples, the control unit is further configured to estimate the axial foreshortening of the frame by multiplying the number of click sounds by the length of a single ratcheting tooth, the evaluation of the expanded diameter being responsive to the estimated axial foreshortening.

In some examples, the evaluation of the expanded diameter is based on pre-stored relationships between axial foreshortening and radial expansion of the frame.

In some examples, the prosthetic valve comprises three expansion and locking assemblies, wherein the control unit is further configured to differentiate between click sounds of different expansion and locking assemblies based on identification of the time difference between such click sounds.

In some examples, the sound sensor is disposed between the actuator and the sleeve.

In some examples, the sound sensor is attached to the actuator.

In some examples, the difference between an inner diameter of the sleeve and an outer diameter of the actuator is at least twice as large as the thickness of the sound sensor.

In some examples, the sleeve has a non-uniform inner diameter such that the difference between the inner diameter of the sleeve and an outer diameter of the actuator is at least twice as large as the thickness of the sound sensor at the region at which the sound sensor is positioned, and wherein the sleeve comprises a neck portion tapering distally inward to a narrower inner diameter of the sleeve.

According to another aspect of the invention, there is provided a delivery assembly comprising a prosthetic valve, a delivery apparatus and at least one vibration sensor. The prosthetic valve comprises a frame movable between a radially compressed configuration and a radially expanded configuration, and at least one expansion and locking assembly. The at least one expansion and locking assembly comprises an outer member coupled to the frame at a first location, and an inner member, coupled to the frame at a second location spaced apart from the first location. The inner member extends at least partially into the outer member, and comprises a plurality of ratcheting teeth.

The delivery apparatus comprises a handle, a delivery shaft extending distally from the handle, and at least one actuation assembly. The at least one actuation assembly comprises an actuator extending from the handle through the delivery shaft, and a sleeve disposed around the corresponding actuator. The actuator is releasably coupled to the corresponding inner member.

The spring biased arm is biased toward the inner member, wherein engagement of the pawl with the ratcheting teeth allows movement in a first direction to allow axial foreshortening and radial expansion of the frame and prevents movement in a second direction to prevent radial compression of the frame.

The at least one vibration sensor is attached to the at least one actuation assembly, and is configured to generate signals commensurate with vibrations generated by the expansion and locking assembly during movement of the pawl over each ratcheting tooth.

In some examples the delivery assembly further comprises a control unit configured to: receive the signals from the at least one vibration sensor; responsive to the received signals, count the vibrations generated by the expansion and locking assembly during movement of the pawl over each ratcheting tooth; responsive to an outcome of the count of the vibrations, evaluate an expanded diameter of the prosthetic valve; and output an indication of the expanded diameter.

In some examples, the control unit is further configured to estimate the axial foreshortening of the frame by multiplying the number of vibrations generated by the expansion and locking assembly during movement of the pawl over each ratcheting tooth, by the length of a single ratcheting tooth, the evaluation of the expanded diameter responsive to the estimated axial foreshortening.

In some examples, the evaluation of the expanded diameter of the prosthetic valve is based on pre-stored relationships between axial foreshortening and radial expansion of the frame.

In some examples, the at least one expansion and locking assembly comprises three expansion and locking assemblies, and wherein the actuation assembly comprises three actuation assemblies, each vibration sensor attached to a separate actuation assembly coupled to corresponding expansion and locking assembly, and wherein the control unit is further configured to identify signals acquired within a predefined time period and mathematically manipulate such signals.

In some examples, the mathematical manipulation comprises averaging the signals received within the predefined time period.

In some examples, the control unit is further configured to identify a non-uniform expansion of the prosthetic valve, the evaluation of the expanded diameter responsive to the identified non-uniform expansion.

In some examples, the identification of a non-uniform expansion comprises estimating the extent of axial foreshortening at more than two regions around the circumference of the prosthetic valve.

In some examples, the identification of a non-uniform expansion comprises estimating the circumferential contour of the expanded prosthetic valve.

In some examples, the vibration sensor is disposed between the actuator and the sleeve, and/or attached to the actuator, and wherein the difference between an inner diameter of the sleeve and an outer diameter of the actuator is at least twice as large as the thickness of the vibration sensor.

In some examples, the vibration sensor is disposed between the actuator and the sleeve, and/or attached to the actuator, and wherein the sleeve has a non-uniform inner diameter such that the difference between the inner diameter of the sleeve and an outer diameter of the actuator is at least twice as large as the thickness of the vibration sensor at the region at which the vibration sensor is positioned, and wherein the sleeve comprises a neck portion tapering distally inward to a narrower inner diameter of the sleeve.

Certain examples of the present invention may include some, all, or none of the above advantages. Further advantages may be readily apparent to those skilled in the art from the figures, descriptions, and claims included herein. Aspects and examples of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following examples and aspects thereof are described and illustrated in conjunction with systems, tools and methods which are meant to be exemplary and illustrative, but not limiting in scope. In various examples, one or more of the above-described problems have been reduced or eliminated, while other examples are directed to other advantages or improvements.

BRIEF DESCRIPTION OF THE FIGURES

Some examples of the invention are described herein with reference to the accompanying figures. The description, together with the figures, makes apparent to a person having ordinary skill in the art how some examples may be practiced. The figures are for the purpose of illustrative description and no attempt is made to show structural details of an example in more detail than is necessary for a fundamental understanding of the invention. For the sake of clarity, some objects depicted in the figures are not to scale.

In the Figures:

FIGS. 6A-6B show enlarged cross-sectional views of ratcheting teeth of an inner member sliding over a pawl of a spring-biased arm, according to some examples.

DETAILED DESCRIPTION OF SOME EXAMPLES

Figure 1:
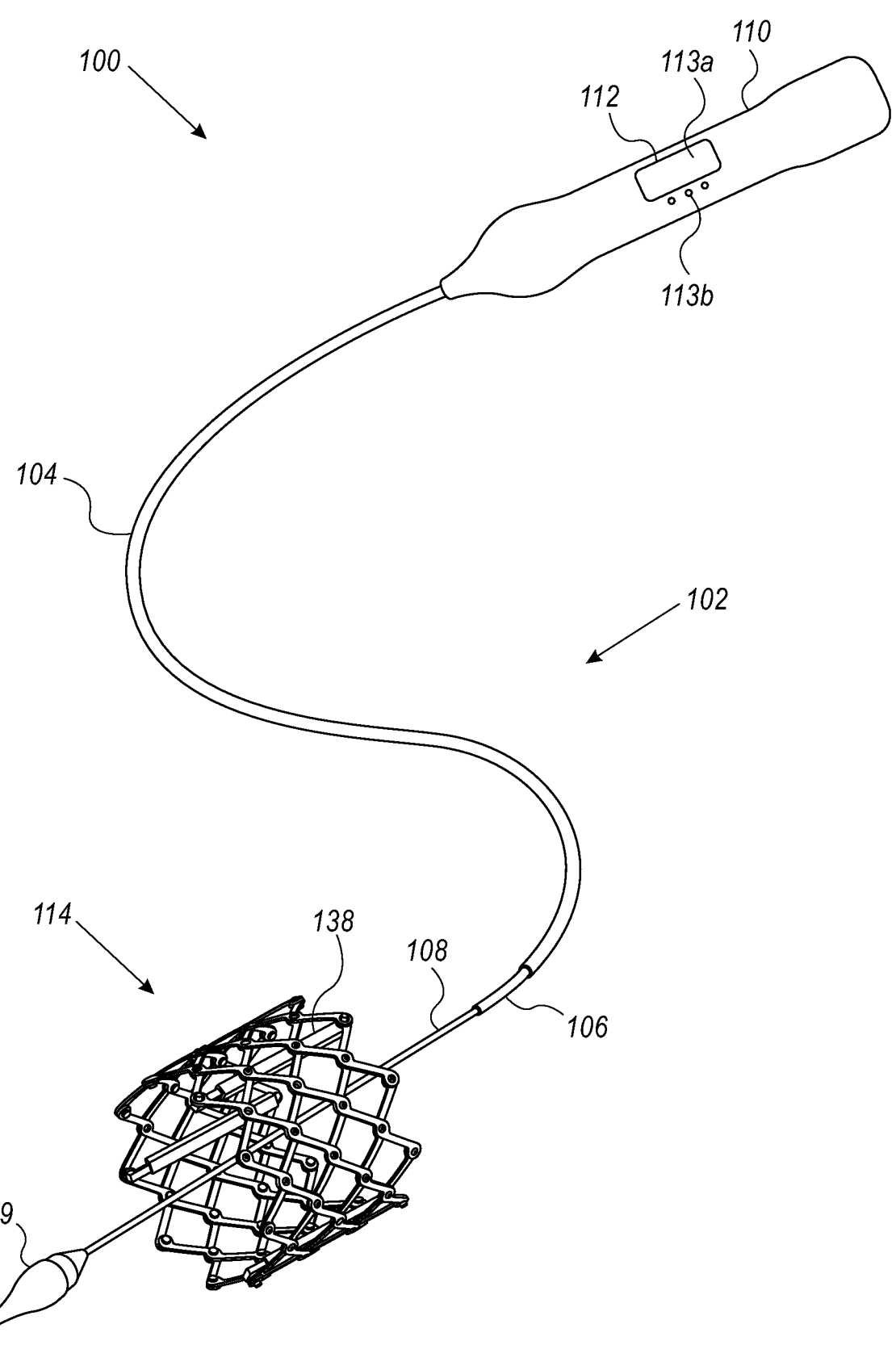
FIG. 1 shows a view in perspective of a delivery assembly comprising a delivery apparatus carrying a prosthetic valve, according to some examples.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Throughout the figures of the drawings, different superscripts for the same reference numerals are used to denote different examples of the same elements. Examples of the disclosed devices and systems may include any combination of different examples of the same elements. Specifically, any reference to an element without a superscript may refer to any alternative example of the same element denoted with a superscript. In order to avoid undue clutter from having too many reference numbers and lead lines on a particular drawing, some components will be introduced via one or more drawings and not explicitly identified in every subsequent drawing that contains that component.

FIG. 1 shows a view in perspective of a delivery assembly 100, according to some examples. The delivery assembly 100 can include a prosthetic valve 114 and a delivery apparatus 102. The prosthetic valve 114 can be on or releasably coupled to the delivery apparatus 102. The delivery apparatus can include a handle 110 at a proximal end thereof, a nosecone shaft 108 extending distally from the handle 110, a nosecone 109 attached to the distal end of the nosecone shaft 108, a delivery shaft 106 extending over the nosecone shaft 108, and optionally an outer shaft 104 extending over the delivery shaft 106.

The term "proximal", as used herein, generally refers to the side or end of any device or a component of a device, which is closer to the handle 110 or an operator of the handle 110 when in use.

The term "distal", as used herein, generally refers to the side or end of any device or a component of a device, which is farther from the handle 110 or an operator of the handle 110 when in use.

The term "prosthetic valve", as used herein, refers to any type of a prosthetic valve deliverable to a patient's target site over a catheter, which is radially expandable and compressible between a radially compressed, or crimped, state, and a radially expanded state. Thus, a prosthetic valve 114 can be crimped or retained by a delivery apparatus 102 in a compressed state during delivery, and then expanded to the expanded state once the prosthetic valve 114 reaches the implantation site. The expanded state may include a range of diameters to which the valve may expand, between the compressed state and a maximal diameter reached at a fully expanded state. Thus, a plurality of partially expanded states may relate to any expansion diameter between radially compressed or crimped state, and maximally expanded state.

The term "plurality", as used herein, means more than one.

A prosthetic valve 114 of the current disclosure may include any prosthetic valve configured to be mounted within the native aortic valve, the native mitral valve, the native pulmonary valve, and the native tricuspid valve. While a delivery assembly 100 described in the current disclosure, includes a delivery apparatus 102 and a prosthetic valve 114, it should be understood that the delivery apparatus 102 according to any example of the current disclosure can be used for implantation of other prosthetic devices aside from prosthetic valves, such as stents or grafts.

According to some examples, the prosthetic valve 114 is a mechanically expandable valve, and the delivery apparatus 102 further comprises a plurality of actuation assemblies 170 (shown, for example, in FIGS. 3 and 4C) extending from the handle 110 through the delivery shaft 106. The actuation assemblies 170 can generally include actuators 172 (visible, for example, in FIGS. 7A-7C) releasably coupled at their distal ends to respective expansion and locking assemblies 138 of the valve 114, and sleeves 176 disposed around the respective actuators 172. Each actuator 172 may be axially movable relative to the sleeve 176 covering it.

The prosthetic valve 114 can be delivered to the site of implantation via a delivery assembly 100 carrying the valve 114 in a radially compressed or crimped state, toward the target site, to be mounted against the native anatomy, by expanding the valve 114 via a mechanical expansion mechanism, as will be elaborated below.

The delivery assembly 100 can be utilized, for example, to deliver a prosthetic aortic valve for mounting against the aortic annulus, to deliver a prosthetic mitral valve for mounting against the mitral annulus, or to deliver a prosthetic valve for mounting against any other native annulus.

The nosecone 109 can be connected to the distal end of the nosecone shaft 108. A guidewire (not shown) can extend through a central lumen of the nosecone shaft 108 and an inner lumen of the nosecone 109, so that the delivery apparatus 102 can be advanced over the guidewire through the patient's vasculature.

As mentioned above, the proximal ends of the nosecone shaft 108, the delivery shaft 106, components of the actuation assemblies 170, and when present—the outer shaft 104, can be coupled to the handle 110. During delivery of the prosthetic valve 114, the handle 110 can be maneuvered by an operator (e.g., a clinician or a surgeon) to axially advance or retract components of the delivery apparatus 102, such as the nosecone shaft 108, the delivery shaft 106, and/or the outer shaft 104, through the patient's vasculature, as well as to expand or contract the prosthetic valve 114, for example by maneuvering the actuation assemblies 170, and to disconnect the prosthetic valve 114 from the delivery apparatus 102, for example—by decoupling the actuators 172 from the expansion and locking assemblies 138 of the valve 114, in order to retract it once the prosthetic valve is mounted in the implantation site.

The term "and/or" is inclusive here, meaning "and" as well as "or". For example, "delivery shaft 106 and/or outer shaft 104" encompasses, delivery shaft 106, outer shaft 104, and delivery shaft 106 with outer shaft 104; and, such "delivery shaft 106 and/or outer shaft 104" may include other elements as well.

According to some examples, the handle 110 can include one or more operating interfaces, such as steerable or rotatable adjustment knobs, levers, sliders, buttons (not shown) and other actuating mechanisms, which are operatively connected to different components of the delivery apparatus 102 and configured to produce axial movement of the delivery apparatus 102 in the proximal and distal directions, as well as to expand or contract the prosthetic valve 114 via various adjustment and activation mechanisms.

According to some examples, the handle 110 further comprises one or more visual or auditory informative elements (such as display 112) configured to provide visual or auditory information and/or feedback to a user or operator of the delivery apparatus 102, such as a LCD screen 113*a*, LED lights 113*b*, speakers (not shown) and the like.

Figures 2, 3:
FIGS. 2 and 3 are views in perspective of a mechanically expandable prosthetic valve with and without soft components of the valve, respectively, according to some examples.

FIG. 2 shows an example of a mechanically expandable prosthetic valve 114 in an expanded state, according to some examples. FIG. 3 shows the prosthetic valve 114 of FIG. 2 with actuation assemblies 170 coupled to the expansion and locking assemblies 138. Soft components, such as leaflets or skirts, are omitted from view in FIG. 3 to expose the expansion and locking assemblies 138. The prosthetic valve 114 can comprise an inflow end portion 118 defining an inflow end 119, and an outflow end portion 116 defining an outflow end 117. In some instances, the outflow end 117 is the distal end of the prosthetic valve 114, and the inflow end 119 is the proximal end of the prosthetic valve 114. Alternatively, depending for example on the delivery approach of the valve, the outflow end can be the proximal end of the prosthetic valve, and the inflow end can be the distal end of the prosthetic valve.

The term "outflow", as used herein, refers to a region of the prosthetic valve through which the blood flows through and out of the valve 114.

The term "inflow", as used herein, refers to a region of the prosthetic valve through which the blood flows into the valve 114.

The valve 114 comprises a frame 120 composed of interconnected struts 122, and may be made of various suitable materials, such as stainless steel, cobalt-chrome alloy (e.g. MP35N alloy), or nickel titanium alloy such as Nitinol. According to some examples, the struts 122 are arranged in a lattice-type pattern. In the example illustrated in FIGS. 2-3, the struts 122 are positioned diagonally, or offset at an angle relative to, and radially offset from, the longitudinal axis of the valve 114, when the valve 114 is in an expanded position. It will be clear that the struts 122 can be offset by other angles than those shown in FIGS. 2-3, such as being oriented substantially parallel to the longitudinal axis of the valve.

According to some examples, the struts 122 are pivotably coupled to each other. In the example shown in FIGS. 2-3, the end portions of the struts 122 are forming apices 126 at the outflow end 117 and apices 128 at the inflow end 119. The struts 122 can be coupled to each other at additional junctions 124 formed between the outflow apices 126 and the inflow apices 128. The junctions 124 can be equally spaced apart from each other, and/or from the apices 126, 128 along the length of each strut 122. Frame 120 may comprise openings or apertures at the regions of apices 126, 128 and junctions 124 of the struts 122. Respective hinges can be included at locations where the apertures of struts 122 overlap each other, via fasteners such as rivets or pins, which extend through the apertures. The hinges can allow the struts 122 to pivot relative to one another as the frame 120 is radially expanded or compressed.

In alternative examples, the struts are not coupled to each other via respective hinges, but are otherwise pivotable or bendable relative to each other, so as to permit frame expansion or compression. For example, the frame can be formed from a single piece of material, such as a metal tube, via various processes such as, but not limited to, laser cutting, electroforming, and/or physical vapor deposition, while retaining the ability to collapse/expand radially in the absence of hinges and like.

The frame 120 further comprises a plurality of cells 130, defined between intersecting portions of struts 122. The shape of each cell 130, and the angle between each portions of struts 122 defining its borders, vary during expansion or compression of the prosthetic valve 114.

The prosthetic valve 114 further comprises a leaflet assembly 132 having one or more leaflets 133, e.g., three leaflets, configured to regulate blood flow through the prosthetic valve 114 from the inflow end to the outflow end. While three leaflets 133 configured to collapse in a tricuspid arrangement similar to the native aortic valve, are shown in the example illustrated in FIG. 2, it will be clear that a prosthetic valve 114 can include any other number of leaflets 133, such as two leaflets configured to collapse in a bicuspid arrangement similar to the native mitral valve, or more than three leaflets, depending upon the particular application. The leaflets 133 are made of a flexible material, derived from biological materials (e.g., bovine pericardium or pericardium from other sources), bio-compatible synthetic materials, or other suitable materials as known in the art and described, for example, in U.S. Pat. Nos. 6,730,118, 6,767, 362 and 6,908,481, which are incorporated by reference herein.

The leaflets 133 may be coupled to the frame 120 via commissures 134, either directly or attached to other structural elements connected to the frame 120 or embedded therein, such as commissure posts. Further details regarding prosthetic valves, including the manner in which leaflets may be mounted to their frames, are described in U.S. Pat. Nos. 7,393,360, 7,510,575, 7,993,394 and 8,252,202, and U.S. Patent Application No. 62/614,299, all of which are incorporated herein by reference.

According to some examples, the prosthetic valve 114 may further comprise at least one skirt or sealing member, such as the inner skirt 136 shown in the example illustrated in FIG. 2. The inner skirt 136 can be mounted on the inner surface of the frame 120, configured to function, for example, as a sealing member to prevent or decrease perivalvular leakage. The inner skirt 136 can further function as an anchoring region for the leaflets 133 to the frame 120, and/or function to protect the leaflets 133 against damage which may be caused by contact with the frame 120, for example during valve crimping or during working cycles of the prosthetic valve 114. Additionally, or alternatively, the prosthetic valve 114 can comprise an outer skirt (not shown) mounted on the outer surface of the frame 120, configure to function, for example, as a sealing member retained between the frame 120 and the surrounding tissue of the native annulus against which the prosthetic valve 114 is mounted, thereby reducing risk of paravalvular leakage past the prosthetic valve 114. Any of the inner skirt 136 and/or outer skirt can be made of various suitable biocompatible materials, such as, but not limited to, various synthetic materials (e.g., PET) or natural tissue (e.g. pericardial tissue).

Figures 4A, 4B:
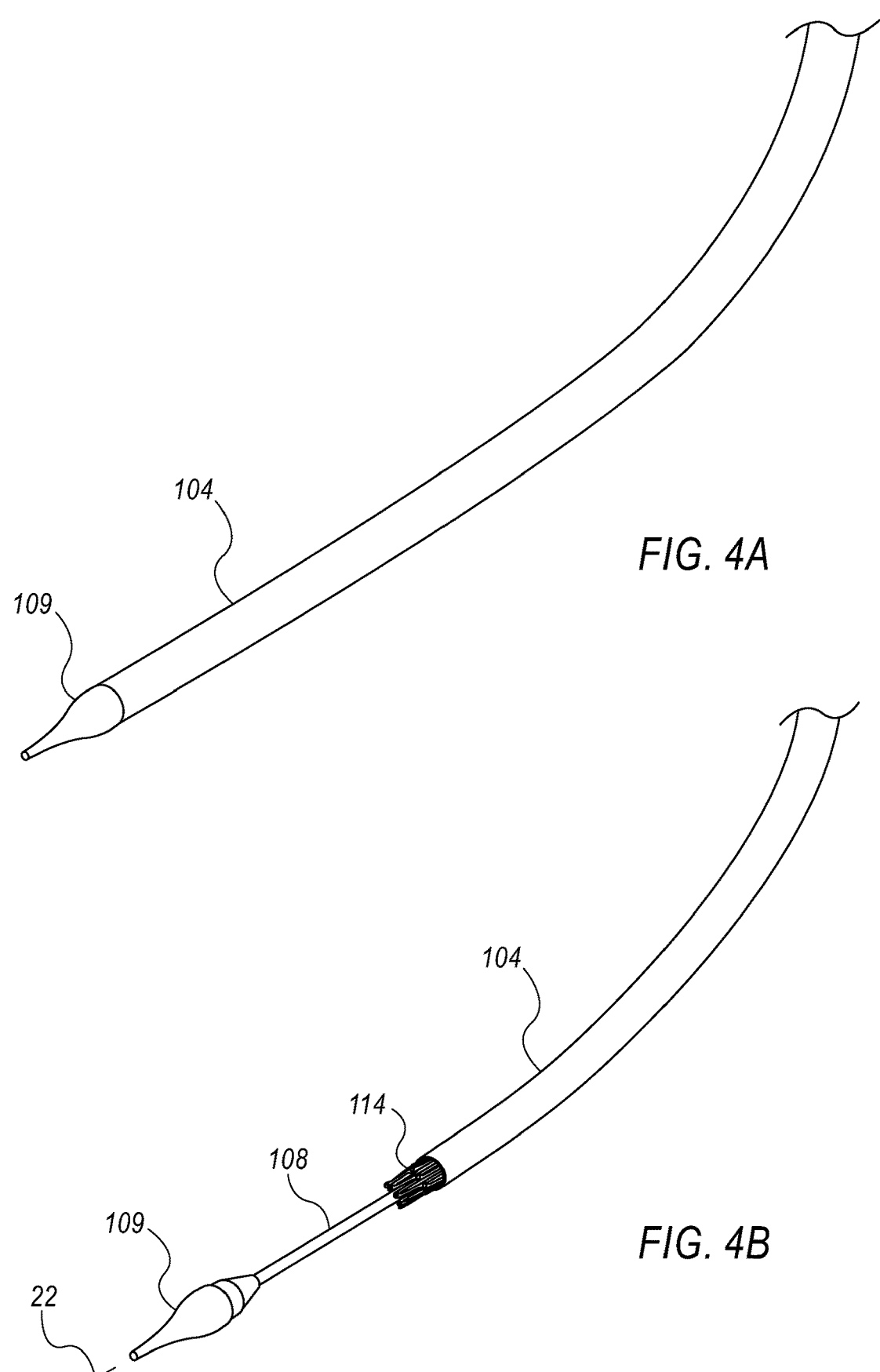
FIGS. 4A-4C show the distal portion of a delivery assembly at different stages of a prosthetic valve delivery and expansion procedure, according to some examples.
Figures 4C, 5A:
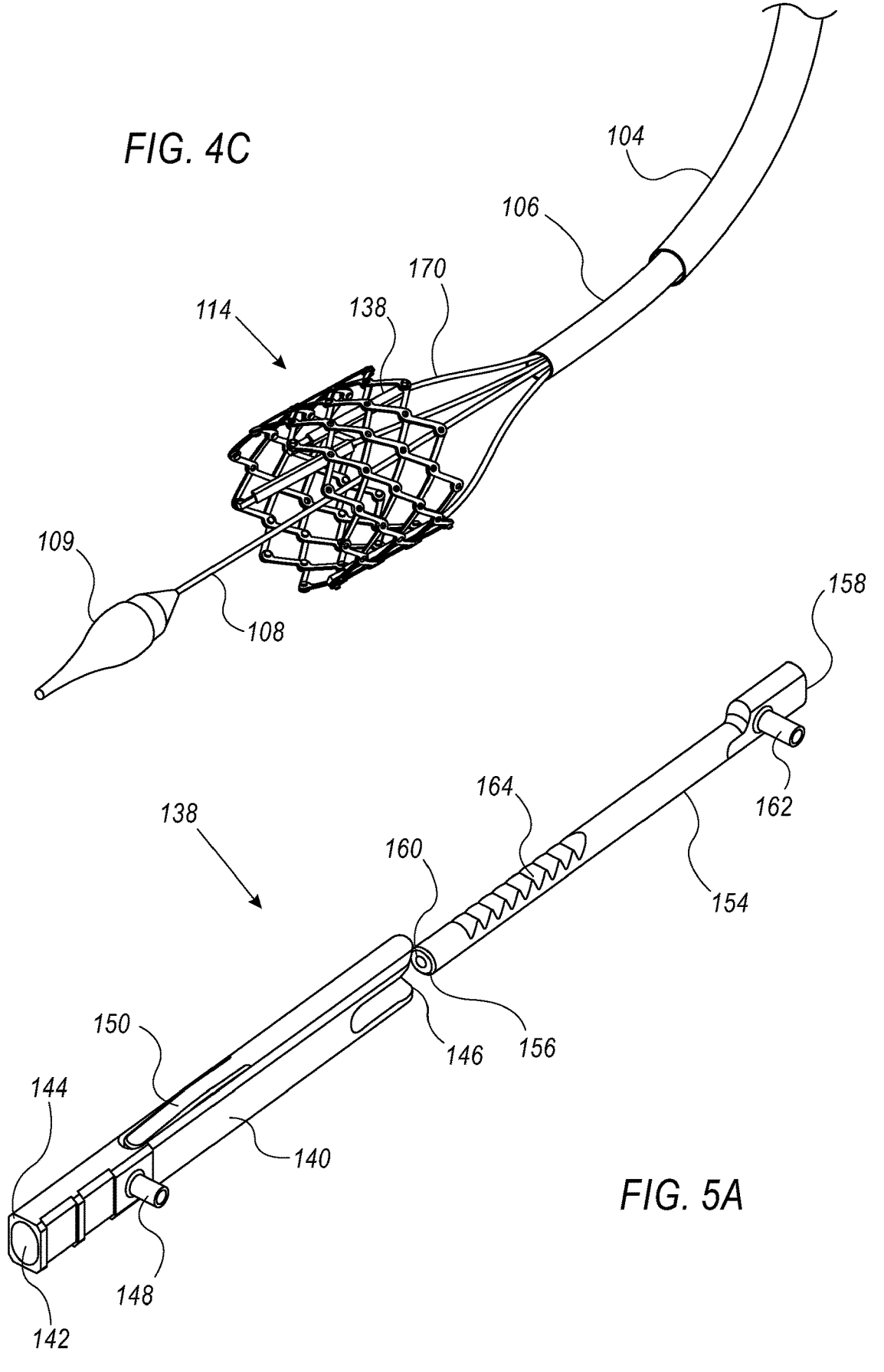
FIGS. 5A-5C show an exploded view in perspective, an assembled view in perspective, and a cross-sectional side view, respectively, of an expansion and locking assembly, according to some examples.

FIGS. 4A-4C show the distal portion of the delivery assembly 100 at different stages of a prosthetic valve 114 delivery and expansion procedure. Prior to implantation, the prosthetic valve 114 can be crimped onto the delivery apparatus 102. This step can include placement of the radially compressed valve 114 within the outer shaft 104. A distal end portion of the outer shaft 104 can extend over the prosthetic valve 114 and contact the nosecone 109 in a delivery configuration of the delivery apparatus 102. Thus, the distal end portion of the outer shaft 104 can serve as a delivery capsule that contains, or houses, the prosthetic valve 114 in a radially compressed or crimped configuration for delivery through the patient's vasculature. FIG. 4A shows an example of a distal portion of the outer shaft 104 extending over a crimped prosthetic valve (hidden from view), having the distal lip of the outer shaft pressed against the nosecone.

The outer shaft 104 and the delivery shaft 106 can be configured to be axially movable relative to each other, such that a proximally oriented movement of the outer shaft 104 relative to the delivery shaft 106, or a distally oriented movement of the delivery shaft 106 relative to the outer shaft 104, can expose the prosthetic valve 114 from the outer shaft 104 as shown in FIG. 4B. In alternative examples, the prosthetic valve 114 is not housed within the outer shaft 104 during delivery. Thus, according to some examples, the delivery apparatus 102 does not include an outer shaft 104.

FIG. 4C shows a fully exposed mechanically expandable valve 114 in an expanded state, wherein the distal portions of the actuation assemblies 170, extending from the handle 110 through the delivery shaft 106, are exposed as well.

Figures 5B, 5C:
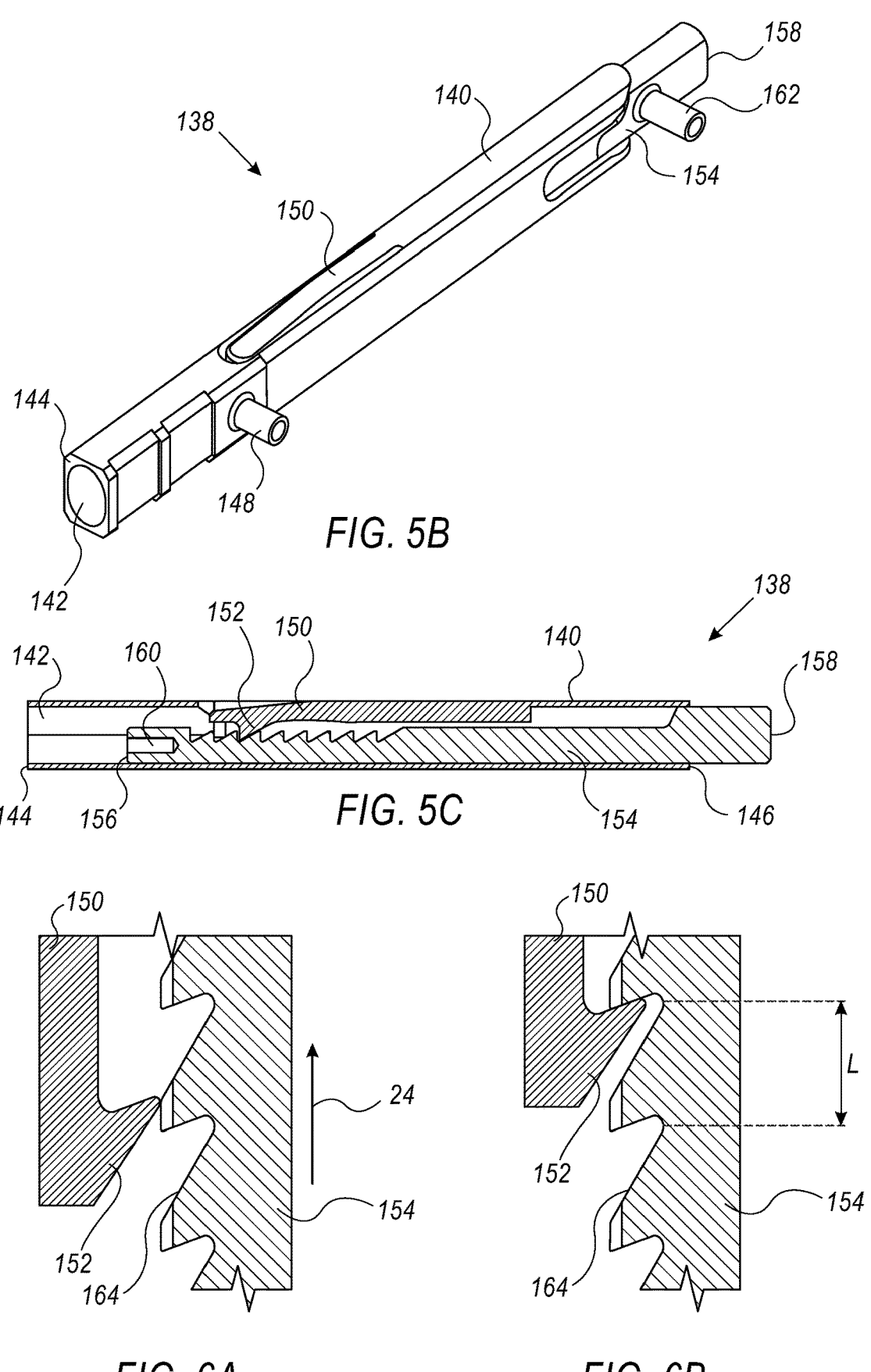

FIGS. 5A, 5B and 5C show an exploded view in perspective, an assembled view in perspective, and a cross-sectional side view, respectively, of an expansion and locking assembly 138 according to some examples. The expansion and locking assembly 138 may include an outer member 140 defining an outer member lumen 142, secured to a component of the valve 114, such as the frame 120, at a first location, and an inner member 154 secured to a component of the valve 114, such as the frame 120, at a second location, axially spaced from the first location.

The inner member 154 extends between an inner member proximal end portion 156 and an inner member distal end portion 158. The inner member 154 comprises an inner member coupling extension 162 extending from its distal end portion 158, which may be formed as a pin extending radially outward from the distal end portion 158, configured to be received within respective openings or apertures of struts 122 intersecting at a junction 124 or an apex 126, 128. The inner member 154 may further comprise a linear rack having a plurality of ratcheting teeth 164 along at least a portion of its length. According to some examples, inner member 154 further comprises a plurality of ratcheting teeth 164 along a portion of its outer surface.

The outer member 140 comprises an outer member proximal end portion 144 defining a proximal opening of its lumen 142, and an outer member distal end portion 146 defining a distal opening of its lumen 142. The outer member 140 can further comprise an outer member coupling extension 148 extending from its proximal end portion 144, which may be formed as a pin extending radially outward from the external surface of the proximal end portion 144, configured to be received within respective openings or apertures of struts 122 intersecting at a junction 124 or an apex 126, 128.

The outer member 140 can further comprise a spring biased arm 150, attached to or extending from one sidewall of the outer member 140, and having a tooth or pawl 152 at its opposite end, biased inward toward the inner member 154 when disposed within the outer member lumen 142.

At least one of the inner or outer member 154 or 140, respectively, is axially movable relative to its counterpart. The expansion and locking assembly 138 in the illustrated example, comprises a ratchet mechanism or a ratchet assembly, wherein the pawl 152 is configured to engage with the teeth 164 of the inner member 154. The spring-biased arm 150 can comprise an elongate body terminating in a pawl 152 in the form of a locking tooth, configured to engage the ratcheting teeth 164 of the inner member 154. As shown in FIGS. 6A-6B, the pawl 152 can have a shape that is complimentary to the shape of the teeth 164, such that the pawl 152 allows sliding movement of the inner member 154 in one direction relative to the spring-biased arm 150 (proximal direction in the illustrated example, as shown by arrow 24) and resists sliding movement of the inner member 154 in the opposite direction (distal direction in the illustrated example) when the pawl 152 is in engagement with one of the teeth 164.

Referring again to FIG. 5C, the arm 150 can be biased inwardly such that the pawl 152 is resiliently retained in a position engaging one of the teeth 164 of the inner member 154 (which can be referred to as the engaged position of the pawl 152). In the illustrated example, the spring-biased arm 150 is implemented as a leaf spring. In some examples, the spring-biased arm 150 can be integrally formed with the outer member 140, in other examples, the spring-biased arm 150 can be separately formed and subsequently coupled to the outer member 140. The biased configuration of the arm 150 ensures that under normal operation, the pawl 152 stays engaged with the teeth 164 of the inner member 154.

The spring biased arm 150 can be formed of a flexible or resilient portion of the outer member 140 that extends over and contacts, via its pawl 152, an opposing side of the outer surface of the inner member 154. According to some examples, the spring biased arm 150 can be formed from a shape-memory material (e.g., Nitinol) pre-treated (for example, by implementing heat-treatment processes) to assume a biased configuration.

A mechanically expandable prosthetic valve 114 may be releasably attachable to at least one actuation assembly 170, and preferably a plurality of actuation assemblies 170, matching the number of expansion and locking assemblies 138. In some examples, the prosthetic valve 114 comprises three expansion and locking assemblies 138, and the delivery apparatus comprises three actuation assemblies 170. The actuator 172 and the sleeve 176 can be movable longitudinally relative to each other in a telescoping manner to radially expand and contract the frame 120, as further described in U.S. Publication Nos. 2018/0153689, 2018/0153689 and 2018/0325665, which are incorporated herein by reference. The actuators 172 can be, for example, wires, cables, rods, or tubes. The sleeves 176 can be, for example, tubes or sheaths having sufficient rigidity such that they can apply a distally directed force to the frame 120 or the outer member 140 without bending or buckling.

The inner member proximal end portion 156 further comprises an inner member threaded bore 160, configured to receive and threadedly engage with a threaded portion of a distal end portion 174 (shown for example in FIG. 7C) of a corresponding actuator 172. FIG. 3 shows a view in perspective of a valve 114 in an expanded state, having its expansion and locking assemblies 138 connected to actuators 172 (hidden from view within the sleeves 176) of a delivery apparatus 102. When actuators 172 are threaded into the inner members 154, axial movement of the actuators 172 causes axial movement of the inner members 154 in the same direction.

Figure 7A:
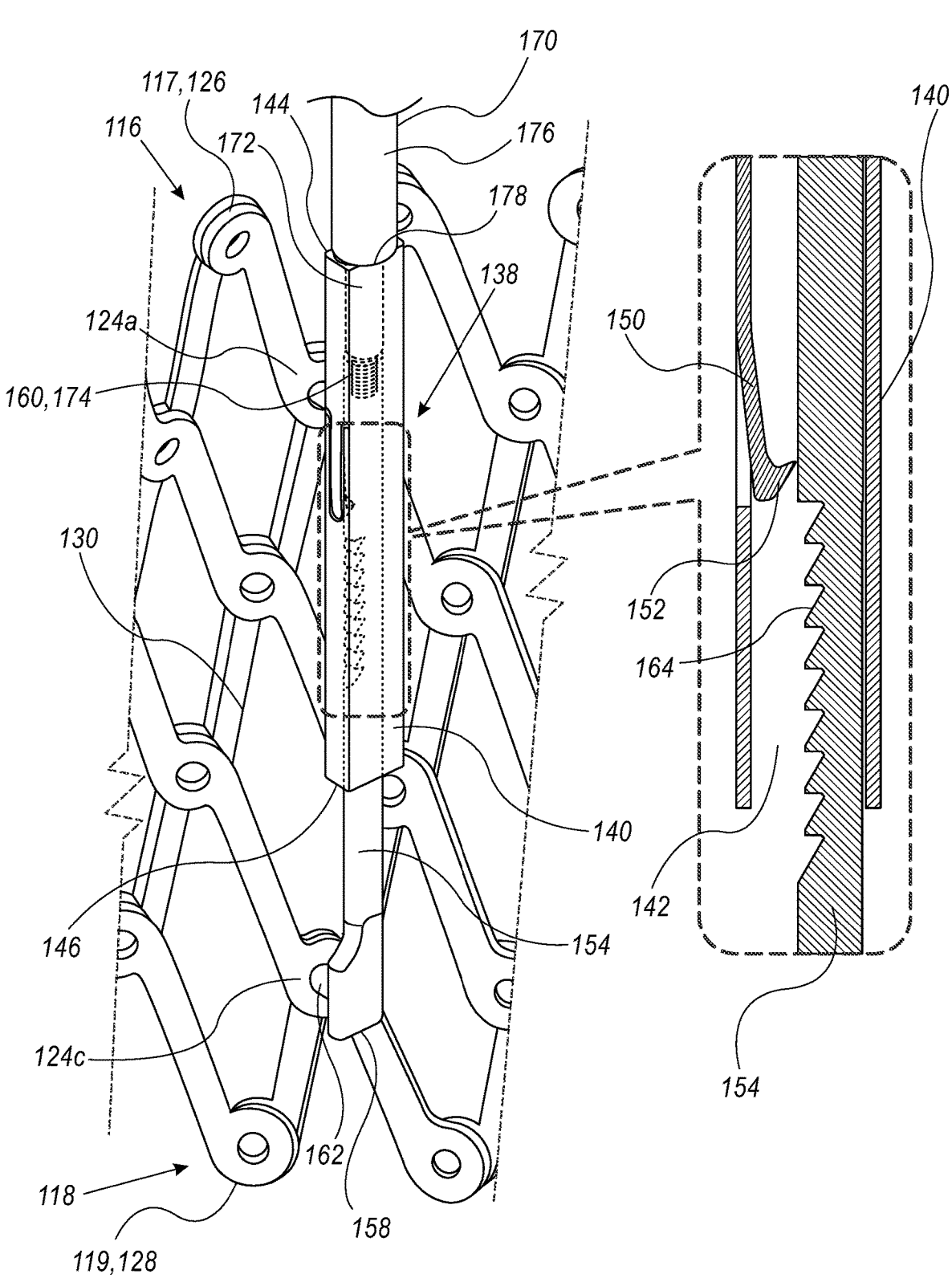
FIGS. 7A-7C show stages of actuating an expansion and locking assembly by an actuation assembly to expand a prosthetic valve from a radially compressed configuration to a radially expanded configuration, according to some examples.
Figure 7B:
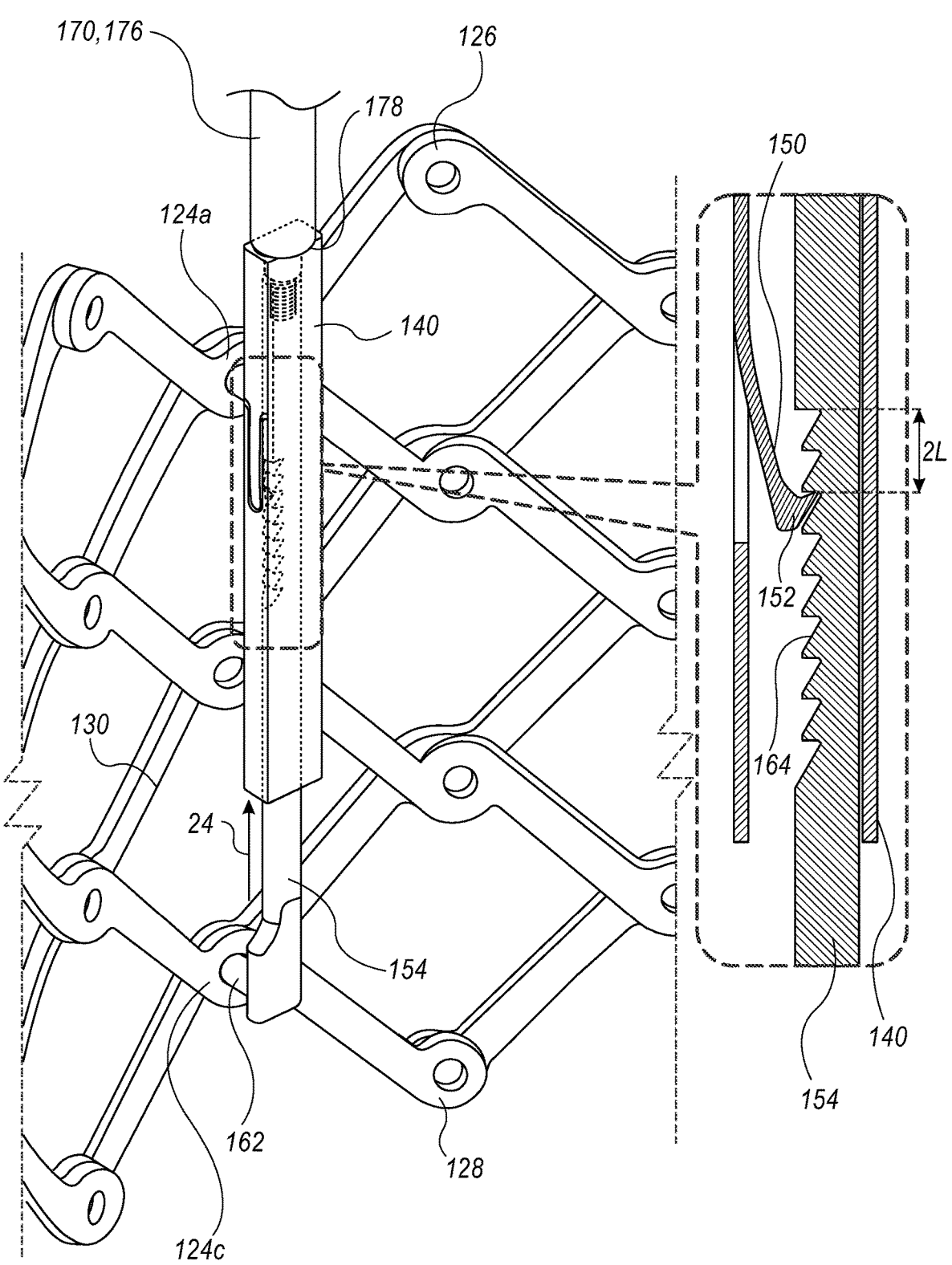
Figure 7C:
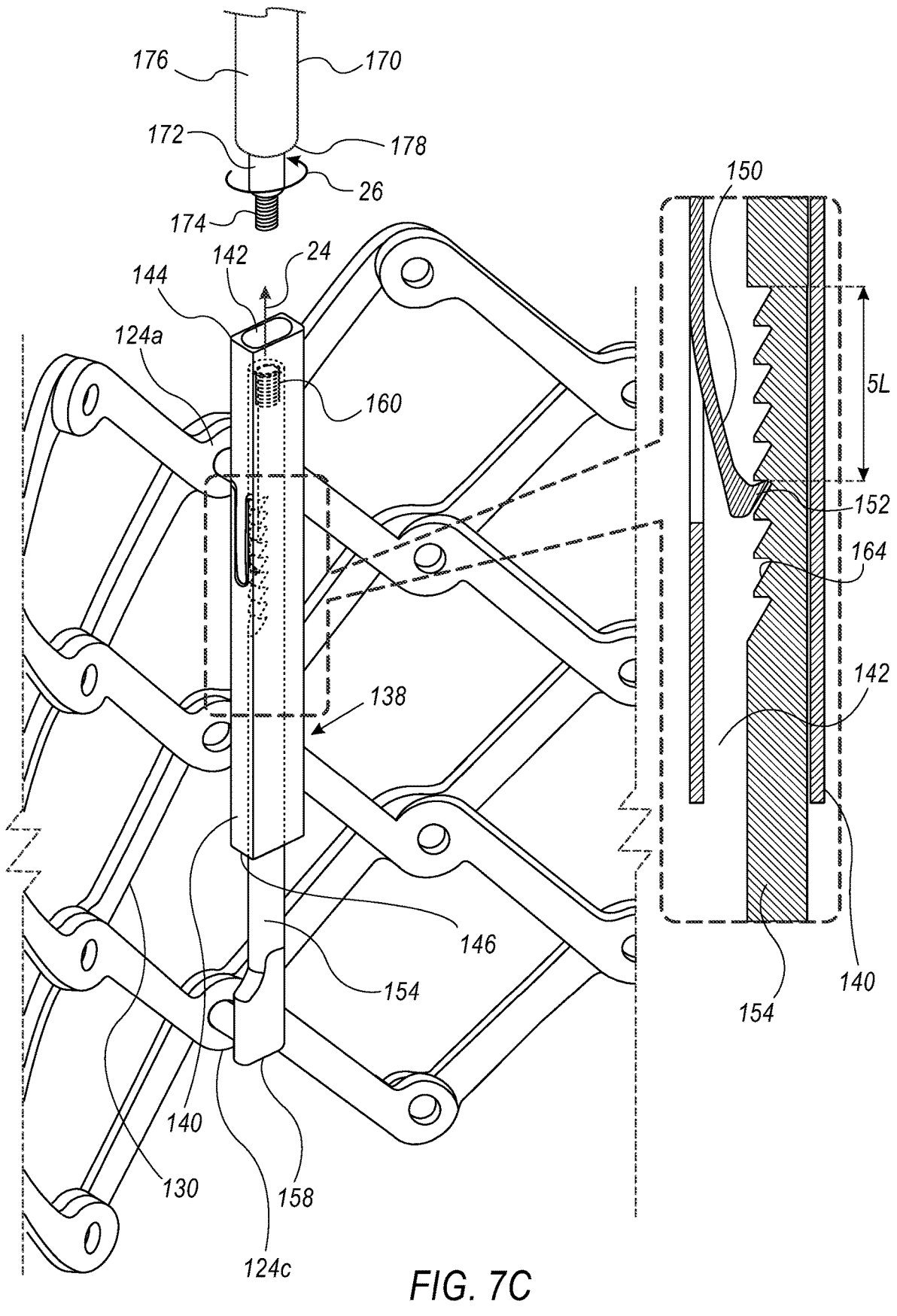

According to some examples, the actuation assemblies 170 are configured to releasably couple to the prosthetic valve 114, and to move the prosthetic valve 114 between the radially compressed and the radially expanded configurations. FIGS. 7A-7C illustrate a non-binding configuration representing actuation of the expansion and locking assemblies 138 via the actuation assemblies 170 to expand the prosthetic valve 114 from a radially compressed configuration to a radially expanded configuration.

FIG. 7A shows an expansion and locking assembly 138, having an outer member 140, secured to the frame 120 at a first location, and an inner member 154 secured to the frame 120 at a second location. According to some examples, the first location can be positioned at or adjacent to the outflow end portion 116, and the second location can be positioned at or adjacent to the inflow end portion 118. In the illustrated example, the outer member 140 is secured to a proximal-most non-apical junction 124a which is distal to the outflow apices 126 or the outflow end 117, via outer member coupling extension 148, and the inner member 154 is secured to a distal-most non-apical junction 124c which is proximal to the inflow apices 128 or the inflow end 119, via inner member coupling extension 162. A proximal portion of the inner member 154 extends, through the distal opening of the outer member distal end 146, into the outer member lumen 142.

It is to be understood that while the illustrated examples are for an expansion and locking assembly 138 secured to a proximal-most non-apical junction 124a serving as the first location, and to a distal-most non-apical junction 124c serving as the second location, in other implementations, the expansion and locking assembly 138 can be secured to other junctions, including apices of the valve. For example, the expansion and locking assembly can be secured to an outflow apex 126 via the outer member coupling extension 148, serving as the first location, and to an opposing inflow apex 128 along the same column of cells, via the inner member coupling extension 162, serving as the second location.

The expansion and locking assembly 138 is shown in FIG. 7A in a radially compressed state of the valve 114, wherein the outflow and inflow apices 126 and 128, respectively, are relatively distanced apart from each other along the axial direction, and the inner member proximal end portion 156 is positioned distal to the outer member proximal end portion 144.

As further shown in FIG. 7A, the actuator distal end portion 174 is threadedly engaged with the inner member threaded bore 160. According to some examples, as shown in FIGS. 7A-7C, the actuator distal end portion 174 includes external threads, configured to engage with internal threads of the inner member threaded bore 160. According to alternative examples, an inner member may include a proximal extension provided with external threads, configured to be received in and engage with internal threads of a distal bore formed within the actuator (examples not shown).

The sleeve 176 surrounds the actuator 172 and may be connected to the handle 110 of a delivery apparatus 102. The sleeve 176 and the outer member 140 are sized such that the distal lip 178 of the sleeve 176 can abut or engage the outer member proximal end 144, such that the outer member 140 is prevented from moving proximally beyond the sleeve 176.

In order to radially expand the frame 120, and therefore the valve 114, the sleeve 176 can be held firmly against the outer member 140. The actuator 172 can then be pulled in a proximally oriented direction 24, as shown in FIG. 7B. Because the sleeve 176 is being held against the outer member 140, which is connected to the frame 120 at the first location, the outflow end 117 of the frame 120 is prevented from moving relative to the sleeve 176. As such, movement of the actuator 172 in a proximally oriented direction 24 can cause movement of the inner member 154 in the same direction, thereby causing the frame 120 to foreshorten axially and expand radially.

More specifically, as shown for example in FIG. 7B, the inner member coupling extension 162 extends through apertures in two struts 122 interconnected at a distal non-apical junction 124c, while the outer member coupling extension 148 extends through aperture in two struts 122 interconnected at a proximal non-apical junction 124a. As such, when the inner member 154 is moved axially, for example in a proximally oriented direction 24, within the outer member lumen 142, the inner member coupling extension 162 moves along with the inner member 154, thereby causing the portion to which the inner member coupling extension 162 is attached to move axially as well, which in turn causes the frame 120 to foreshorten axially and expand radially.

The struts 122 to which the inner member coupling extension 162 is connected are free to pivot relative to the coupling extension 162 and to one another as the frame 120 is expanded or compressed. In this manner, the inner member coupling extension 162 serves as a fastener that forms a pivotable connection between those struts 122. Similarly, struts 122 to which the outer member coupling extension 148 is connected are also free to pivot relative to the coupling extension 148 and to one another as the frame 120 is expanded or compressed. In this manner, the outer coupling extension 148 also serves as a fastener that forms a pivotable connection between those struts 122.

As mentioned above, when the pawl 152 of the spring biased arm 150 is engaged with the ratcheting teeth 164, the inner member 154 can move in one axial direction, such as the proximally oriented direction 24, but cannot move in the opposite axial direction. This ensures that while the pawl 152 is engaged with the ratcheting teeth 164, the frame 120 can radially expand but cannot be radially compressed. Thus, after the prosthetic valve 114 is implanted in the patient, the frame 120 can be expanded to a desired diameter by pulling the actuator 172. In this manner, the actuation mechanism also serves as a locking mechanism of the prosthetic valve 114.

Once the desired diameter of the prosthetic valve 114 is reached, the actuator 172 may be rotated, for example in rotation direction 26, to unscrew the actuator 172 from the inner member 154, as shown in FIG. 7C. This rotation serves to disengage the distal threaded portion 174 of the actuator 172 from the inner member threaded bore 160, enabling the actuation assemblies 170 to be pulled away, and retracted, together with the delivery apparatus 102, from the patient's body, leaving the prosthetic valve 114 implanted in the patient. The patient's native anatomy, such as the native aortic annulus in the case of transcatheter aortic valve implantation, may exert radial forces against the prosthetic valve 114 that would strive to compress it. However, the engagement between the pawl 152 of the spring biased arm 150 and the ratcheting teeth 164 of the inner member 154 prevents such forces from compressing the frame 120, thereby ensuring that the frame 120 remains locked in the desired radially expanded state.

Thus, the prosthetic valve 114 is radially expandable from the radially compressed state shown in FIG. 7A to the radially expanded state shown in FIG. 7B upon actuating the expansion and locking assemblies 138, wherein such actuation includes approximating the second locations to the first locations of the valve 114. The prosthetic valve 114 is further releasable from the delivery apparatus 102 by decoupling each of the actuation assemblies 170 from each of the corresponding expansion and locking assemblies 138 that were attached thereto.

While the frame 120 is shown above to expand radially outward by axially moving the inner member 154 in a proximally oriented direction 24, relative to the outer member 140, it will be understood that similar frame expansion may be achieved by axially pushing an outer member 140 in a distally oriented direction 22, relative to an inner member 154.

While a threaded engagement is illustrated and described in the above examples, serving as an optional reversible-attachment mechanism between the actuation assemblies 170 and the inner members 154, it is to be understood that in alternative implementations, other reversible attachment mechanisms may be utilized, configured to enable the inner member 154 to be pulled or pushed by the actuation assemblies 170, while enabling disconnection therebetween in any suitable manner, so as to allow retraction of the delivery apparatus from the patient's body at the end of the implantation procedure. For example, the distal end portion of the actuator can include a magnet, and the inner member bore can include a correspondingly magnetic material into which the distal end portion of the actuator can extend.

While a specific actuation mechanism is described above, utilizing a ratcheting mechanism between inner and the outer members of expansion and locking assemblies 138 that are attachable, for example via corresponding coupling extensions, to the frame, other actuation mechanisms may be employed to promote relative movement between inner and outer members of actuation assemblies, for example, based on a ratcheting interaction between other components of the prosthetic valve, such as ratcheting engagement between portions of specific struts of the frame, or between other, potentially integrally formed components, of the frame itself.

Referring again to FIG. 6A-6B, the axial length L of a tooth 164 defines the axial distance by which the inner member moves when the pawl 152 slides between the troughs on both ends of the tooth 164, such that the number of teeth N, multiplied by the tooth length L, corresponds to the range of expansion diameters to which the valve 114 can be expanded, and remain locked in the expanded state by having the pawl 152 engaged with the teeth 164.

Referring again to FIG. 7A-7C, the inner member 154 can comprise a toothless portion extending from a proximal end 144 to the plurality of teeth 164. The toothless portion can be a flat portion of the inner member. The toothless portion is configured to allow bi-directional axial movement (in the distal and proximal directions) of the inner member 154 relative to the outer member 140. This allows the frame 120 to expand and/or contract prior to the engagement of the pawl 152 with the plurality of teeth 164. FIG. 7A shows an initial state in which the pawl 152 is pressed against the toothless portion of the inner member 154, proximal to the teeth 164.

When the inner member 154 is pulled in a proximal direction 24, the pawl 152 slides over the toothless portion of the inner member 154 until it engages the teeth 164. The first, proximal-most trough defined by the teeth 164 represents the minimal expansion diameter at which the valve 114 can be retained in a locked state, without being spontaneously re-compressed. FIG. 7B shows an intermediate state wherein the pawl has been slid over two teeth 164, which is indicative of an axial distance 2 L along which the frame 120 foreshortened, beyond the minimal expansion diameter at which the valve may be locked, also termed minimal expansion diameter. FIG. 7C shows an optional final position of the pawl 152, locked against the teeth 164 pas the fifth tooth, which is indicative of an axial distance 5 L along which the frame 120 foreshortened beyond the minimal expansion diameter, to the final expansion diameter, at which point the actuation assemblies 170 can be disengaged from the valve 114.

The number of teeth is selected to cover the desired range of expansion diameters for the valve 114, ranging from a minimal expansion diameter defined by the first (e.g., proximal-most) tooth, to a maximal expansion diameter that may be defined by engagement of the pawl 152 with the teeth 164 past the last (e.g., distal-most) tooth. This range of expansion diameters corresponds to possible expansion diameters allowable by the ratcheting teeth 164, which may be equal to, or greater than, the range of target diameters of the valve 114, wherein the target diameters refer to a range of desired expansion diameters of the valve 114 within a patient's body, ranging from a minimal target diameter to a maximal target diameter.

In some cases, the target range of diameters is narrower than the range of expansion diameters allowable by the ratcheting mechanism, such that the minimal expansion diameter, at which the pawl 152 is engaged with, or proximal to, the first (e.g., proximal-most) tooth 164, is not greater than the minimal target diameter of the valve 114. Similarly, the maximal expansion diameter, at which the pawl 152 is engaged with, or distal to, the last (e.g., distal-most) tooth 164, is at least as great as the maximal target diameter. For example, while a range of expansion diameters, defined by the number of teeth 164 and the relative position between the pawl 152 and the teeth 164, may be in a range such as 23 mm to 30 mm, it may be that the target diameters are in the range of 26 mm to 29 mm.

In the illustrated examples, the plurality of ratcheting teeth 164 extend along a portion of the length of the inner member 154 adjacent the inner member proximal end portion 156. In other examples, the plurality of ratcheting teeth 164 can extend substantially the entire length of the inner member 154. In still other examples, the plurality of ratcheting teeth 164 can extend a portion of the length of the inner member adjacent the inner member distal end portion 158. The length of each tooth L dictates the resolution of discrete expansion diameters.

The movement of the pawl 152 over the ratcheting teeth 164 generates click sounds as the pawl 152 slides over each tooth 164. Each click sound may be representative of the pawl 152 sliding over a single tooth 164 having a tooth length L, such that several consecutive click sounds generated during the movement of a pawl 152 over ratcheting teeth 164 of a corresponding inner member 154 may be indicative of a relative movement between the inner member 154 relative to the outer member 140 along a distance that can be substantially equal to L multiplied by the number of clicks.

According to some examples, there is provided a prosthetic valve expansion monitoring system 166, comprising a delivery assembly 100 and at least one sound sensor 180, wherein the at least one sound sensor 180 is configured to detect clicking sounds produced by a ratcheting mechanism of an expansion and locking assembly 138 of the prosthetic valve 114 during expansion thereof.

Figures 8, 9:
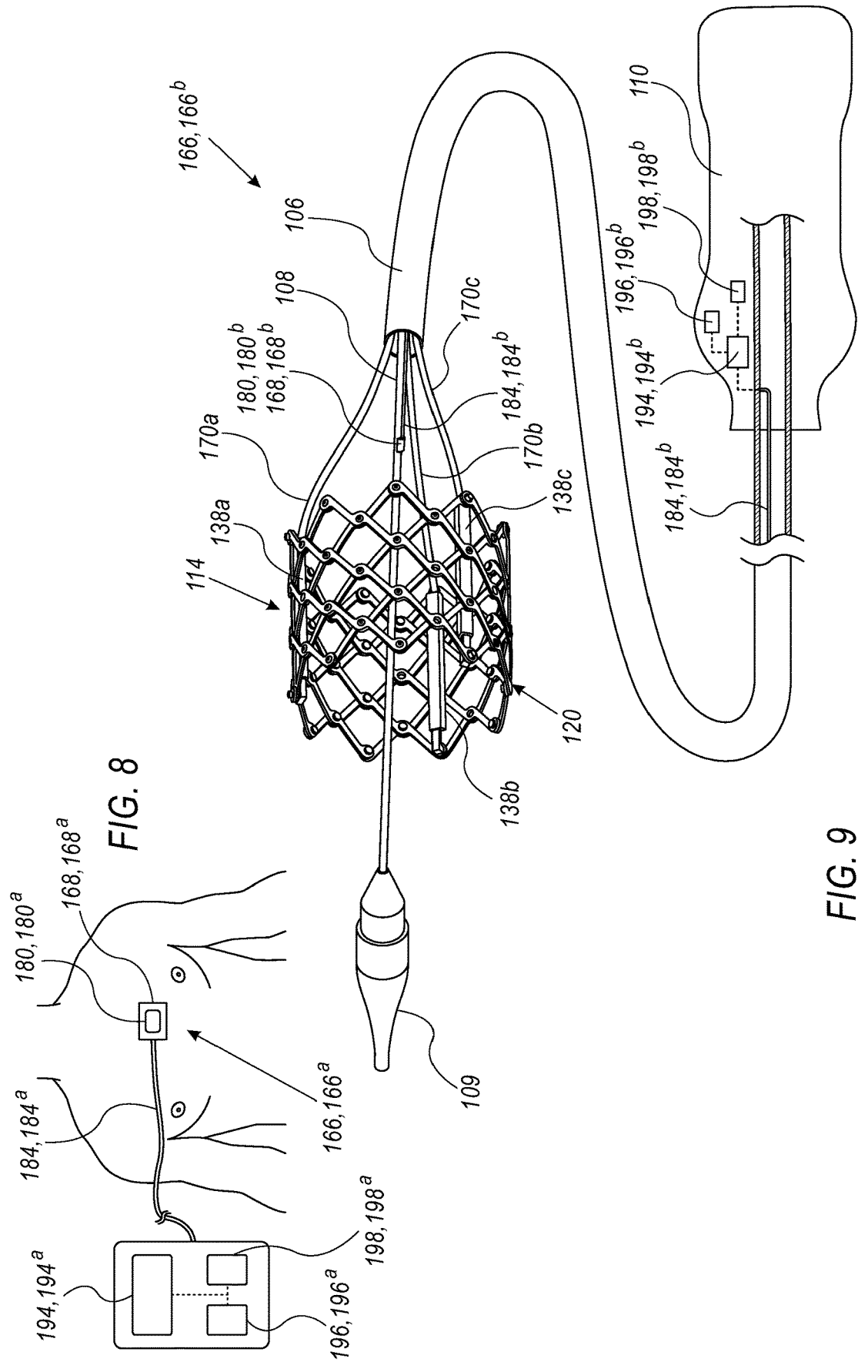
FIG. 8 shows an extracorporeal sound sensor placed over a patient's chest, according to some examples.
FIG. 9 shows an example of a sound sensor attached to a nosecone shaft.

According to some examples, the at least one sound sensor 180 of the monitoring system includes at least one extracorporeal sound sensor 180$^a$. Reference is now made to FIG. 8, showing a schematic example of a prosthetic valve expansion monitoring system 166$^a$ comprising an extracorporeal sound sensor 180$^a$, that can be placed in contact with or in close proximity to the patient's body. According to some examples, the extracorporeal sound sensor 180$^a$ is configured to be placed externally at or in the vicinity of the skin surface of a subject (i.e., a patient), and to externally measure sounds produced within the body of the subject. The extracorporeal sound sensor 180$^a$ can be placed over the patient's chest, as shown in FIG. 8, prior to or during a prosthetic valve implantation procedure.

According to some examples, the at least one sound sensor 180 is comprised within a sensor housing 168. According to some examples, an extracorporeal sound sensor 180$^a$ is comprised within an extracorporeal sensor housing 168$^a$, that can be placed on or attached to the patient's body. In some examples, the extracorporeal sensor housing 168$^a$ can be provided in the form of a patch. In some examples, the extracorporeal sensor housing 168$^a$ is provided in the form of a precordial patch, configured to be placed on or attached to a portion of the patient's body that includes the anterior surface of the lower thorax.

In use, when a prosthetic valve 114 carried by a delivery apparatus 102 is expanded at the implantation site, for example by pulling the actuators 172 in a proximal direction so as to facilitate a relative telescoping movement between the inner members 154 and the outer members 140 of the expansion and locking assemblies 138, a sound sensor 180, such as the extracorporeal sound sensor 180$^a$, is configured to detect click sounds generated during the movement of the pawls 152 over ratcheting teeth 164 of inner members 154 of respective expansion and locking assemblies 138, and to generate signals (e.g., electric signals) commensurate with such click sounds.

According to some examples, the sensor is characterized by having at least one of a high signal-to-noise ratio, high sensitivity, suitable ambient noise shrouding capability, and the ability to measure low frequency signals, in order to overcome various possible disturbances such as background noise or the relatively low amplitude of the vibrations or sounds that are generated by heart activity, lung activity, and/or blood flow.

According to some example, the monitoring system 166 further comprises an ambient noise sensor (not shown) configured to acquire environment noise and/or speech. The ambient noise sensor can be used to remove environmental noise from measured signals. Alternately, any other method of noise removal may additionally or alternatively be used.

According to some examples, the prosthetic valve expansion monitoring system further comprises a control unit 194 configured to receive signals detected by the at least one sound sensor 180. In one example, control unit 194 comprises a processor. In another example, control unit 194 comprises a central processing unit (CPU), a microprocessor, a microcomputer, a programmable logic controller, an application-specific integrated circuit (ASIC) and/or a field-programmable gate array (FPGA), without limitation.

The at least one sound sensor 180 can generate electric signals commensurate with click sounds generated by at least one expansion and locking assembly 138 of the prosthetic valve 114, and to transmit such signals, via wireless or wired communication appliances, for example to a control unit. Wireless communication can include a radio frequency (RF) link, an infrared link, a Bluetooth link, or any other known wireless communication methods. Wired communication can include a communication line 184, attached to the at least one sound sensor 180 at one end, and to a control unit (194) at the other end.

For example, an extracorporeal sound sensor 180$^a$ can be attached to a communication line 184$^a$ configured to transmit signals generated thereby to another extracorporeal component, such as an extracorporeal control unit 194$^a$, wherein the extracorporeal control unit can be coupled to, or in communication with, additional devices or components such as a display module 196 (e.g., extracorporeal display module 196$^a$ shown in FIG. 8) and/or a communication component 198 (e.g., extracorporeal communication component 198$^a$ shown in FIG. 8).

According to some examples, extracorporeal sound sensor 180$^a$ can be configured to detect heart sounds as well as click sounds, and to generate signals that can be distinguished, for example by the control unit 194$_a$. Signals of heart sounds and click sounds can be distinguished from each other due to having, for example, different amplitudes, waveforms and/or frequencies. Heart sound sensors are conventionally utilized for detection of sounds generated by heart activity, which include the opening and closing of the native heart valves and blood flow. The human heart sounds include a first major sound ("S1") and second major sound ("S2"). The first major sound usually includes a mitral valve sound ("M1") and a tricuspid valve sound ("T1"), while the second major sound usually includes an aortic valve sound ("A2") and a pulmonary valve sound ("P2").

Heart sounds, such as S1 and S2, are repetitive sounds generated by the ongoing cycling heart activity, while click sounds of expansion and locking assemblies are non-repetitive sounds that occur only during sliding of a pawl 152 over corresponding ratcheting teeth 164, and will have different amplitudes, waveforms and/or frequencies than those of heart sounds due to being generated by prosthetic, optionally metallic, components interacting with each other.

In some examples, a sound sensor 180, such as extracorporeal sound sensor 180$^a$, is configured to simultaneously measure both heart sounds and click sounds. Electric signals can be transmitted, for example via wireless communication, or via wired communication such as a communication line 184, to control unit 194, which can distinguish between the heart sounds and the click sounds, according to amplitudes, wavelengths and/or frequencies associated with signals of the different types of sounds, as well as according to identification of repetitive vs. non-repetitive sounds. In some examples, extracorporeal sound sensor 180$^a$ is a phonocardiogram sensor.

In some examples, heart sounds monitoring is not required during valve expansion, such that the heart sounds are actually part of background sounds that should be filtered in order to isolate only click sounds.

In some examples, an extracorporeal prosthetic valve expansion monitoring system 166$^a$ further comprises additional sensors, such as ECG sensors (not shown). Such systems can be utilized for measuring, potentially in a simultaneous manner, click sounds and ECG signals, with or without heart sounds. ECG sensors can be embedded within an extracorporeal sensor housing 168$^a$, a precordial patch, or provided as additional sensors that can be placed on or attached to the patient's body.

According to some examples, the delivery assembly 100 comprises the at least one sound sensor, and in particular examples, the at least one sound sensor 180 can be attached to a component of the delivery apparatus 102. Reference is now made to FIGS. 9-13, showing various configurations of prosthetic valve expansion monitoring systems 166, that may include sound sensors 180 comprised within the delivery assembly 100 and/or attached to components of the delivery apparatus 102.

As mentioned hereinabove, the at least one sound sensor 180 can be, in some examples, accommodated within a sensor housing 168. According to some examples, sensor housing 168 can be attached to a component of the delivery apparatus 102 (see FIG. 9). According to still further examples, the sensor housing 168$^b$ comprises at least one biocompatible material. According to still further examples, the sensor housing 1686 is characterized by having a shape and dimensions configured to fit into the delivery apparatus 102.

The biocompatible material can be a biocompatible polymer material selected from but not limited to, poly(dimethyl siloxane) (PDMS), polycaprolactone (PCL), methyl-vinyl siloxane, ethylene/vinyl acetate copolymers, polyethylene, polypropylene, ethylene/propylene copolymers, acrylic acid polymers, ethylene/ethyl acrylate copolymers, polytetrafluoroethylene (PTFE), polyurethanes, thermoplastic polyurethanes and polyurethane elastomers, polybutadiene, polyisoprene, poly(methacrylate), polymethyl methacrylate, styrene-butadiene-styrene block copolymers, poly(hydroxy-ethyl-methacrylate) (pHEMA), polyvinyl chloride, polyvinyl acetate, polyethers, polyacrylo-nitriles, polyethylene glycol (PEG), polymethylpentene, polybutadiene, polyhydroxy alkanoates, poly(lactic acid) (PLA), poly(glycolic acid) (PGA), polyanhydrides, polyorthoesters, and copolymers and combinations thereof.

According to some examples, the at least one sound sensor 180 can be attached to the nosecone shaft 108, the nosecone 109, the delivery shaft 106, the outer shaft 104, the at least one actuation assembly 170 (including attachment to any one of actuator 172 and/or a sleeve 176). According to some examples, the delivery assembly can include a sensor shaft 186 to which the at least one sound sensor 180 is attached. According to some examples, the at least one sound sensor 180 can be attached to an independent catheter 190 that can be advanced toward the implantation site independently of the delivery apparatus. Attachment of the at least one sound sensor 180 to any one of the nosecone shaft 108, the nosecone 109, the delivery shaft 106, the outer shaft 104, the at least one actuation assembly 170, the sensor shaft 186 and/or the independent catheter 190, can be achieved by suturing, screwing, clamping, gluing with biocompatible adhesives, fastening, welding, or any other suitable technique.

According to some examples, the at least one sound sensor 180 comprises a microphone, that can be any of a piezoelectric, a piezoresistive, or a capacitive-type microphone. A piezoelectric microphone may be made from any piezoelectric material, including piezocomposites, piezoceramics, piezoplastics and the like. According to some examples, the least one sound sensor 180 comprises a piezoelectric film, such as polyvinylidine fluoride (PVDF), which takes the form of a thin plastic polymer sheet and may have a thin electrically conductive nickel copper alloy deposited on each side. The sound sensor 180 may act as a strain gage that generates an electrical signal when a diaphragm included therein vibrates in response to sounds. According to some examples, the least one sound sensor 180 is a micro-electrical mechanical system (MEMS) microphone.

FIG. 9 shows an example of a prosthetic valve expansion monitoring system 166$^b$ wherein sound sensor 180$^b$ is attached to the nosecone shaft 108. Preferably, the sound sensor 180$^b$ is attached to a portion of the nosecone shaft 108 that is in the vicinity of the expansion and locking assemblies 138. As shown in FIG. 9, the sound sensor 180$^b$ can be attached to an outer surface of the nosecone shaft 108 at a position that is proximal to the prosthetic valve 114 during valve expansion. However, the sound sensor 180$^b$ can be similarly attached to the outer surface of the nosecone shaft 108 at a position that is either within the internal lumen defined by the prosthetic valve 114, or distal to the prosthetic valve 114, during valve expansion.

It is to be understood that any reference to a sensor, such as any sound sensor 180 or vibration sensor 182, being attached to any component, may refer to the sensor being embedded within a sensor housing 168 that is attached to the corresponding component.

According to some examples, the sound sensor 180$^b$ is attached to a distal portion of the nosecone shaft 108 such that the maximal distance between the sound sensor 180$^b$ and at least one expansion and locking assembly 138, during valve expansion, is not greater than 20 centimeters. According to some examples, the sound sensor 180$^b$ is attached to a distal portion of the nosecone shaft 108 such that the maximal distance between the sound sensor 180$^b$ and at least one expansion and locking assembly 138, during valve expansion, is not greater than 10 centimeters. According to some examples, the sound sensor 180$^b$ is attached to a distal portion of the nosecone shaft 108 such that the maximal distance between the sound sensor 180$^b$ and at least one expansion and locking assembly 138, during valve expansion, is not greater than 5 centimeters.

It is to be understood that the distance between sound sensor 180 and at least one expansion and locking assembly 138 can be measured between a central point of the sound sensor 180 and the pawl 152. In the case of a prosthetic valve 114 provided with a plurality of expansion and locking assemblies 138, this distance can be measured between the sound sensor 180 and the closest pawl 152.

As mentioned above, the sound sensor 180 can be attached to other components of the delivery apparatus 102, besides the nosecone shaft, as will be further elaborated hereinbelow. According to some examples, the sound sensor 180 is attached to a component of the delivery apparatus 102 such that the distance between the sound sensor 180 and the pawl 152 (e.g., the closest pawl in case of a plurality of expansion and locking assemblies), during valve expansion, is not greater than 20 centimeters. According to some examples, the sound sensor 180 is attached to a component of the delivery apparatus 102 such that the distance between the sound sensor 180 and the pawl 152 (e.g., the closest pawl in case of a plurality of expansion and locking assemblies), during valve expansion, is not greater than 10 centimeters.

According to some examples, the sound sensor 180 is attached to a component of the delivery apparatus 102 such that the distance between the sound sensor 180 and the pawl 152 (e.g., the closest pawl in case of a plurality of expansion and locking assemblies), during valve expansion, is not greater than 10 centimeters.

If the sound sensor 180 is attached to a component that may move relative to the pawl 152 during valve expansion, such as being attached to an actuator 172 that may be pulled proximally to pull the inner member 154 during valve expansion, the distance between the sound sensor 180 and the pawl 152 may change during valve expansion. In such cases, the distance should not exceed the above-mentioned values in a state of maximal valve expansion, i.e., when the prosthetic valve 114 is expanded to a maximal desired expansion diameter thereof.

As mentioned hereinabove, the prosthetic valve expansion monitoring system 166 can further comprise a control unit 194, that can receive signals generated by the at least one sound sensor 180, for example via a communication line 184 attached at one end (e.g., the distal end) to the at least one sound sensor 180, and at the opposite end (e.g., the proximal end) to the control unit 194. The communication line 184 can be configured to deliver measurement signals from the at least one sound sensor 180 to the control unit 194, and/or to deliver power to the at least one sound sensor 180.

According to some examples, the at least one sound sensor 180 includes a plurality of sound sensors 180, wherein a matching plurality of communication lines 184 are attached to the sound sensors 180, configured to deliver measurement signals from the sound sensors 180, for example to a control unit 194, and/or to deliver power to the sound sensors 180.

According to some examples, each communication line 184 may include various electrically conductive materials, such as copper, aluminum, silver, gold, and various alloys such as tentalum/platinum, MP35N and the like. An insulator (not shown) can surround each communication line 184. The insulator can include various electrically insulating materials, such as electrically insulating polymers.

The sound sensor 180, according to any example disclosed herein, is configured to generate electric signals representative of sounds detected thereby. Specifically, the sound sensor 180, according to any example disclosed herein, is configured to generate electric signals commensurate with click sounds generated during movement of the pawl 152 of at least one expansion and locking assembly 138 over the ratcheting teeth 164 of the corresponding inner member 154. The communication line 184 is configured to deliver the electric signals to the control unit 194.

According to some examples, the delivery assembly includes the control unit $194^b$. According to some examples, the control unit $194^b$ may be embedded within the handle 110, as schematically illustrated for example in FIG. 9. According to some examples, the communication line 184 is connected to a power source, for example within the handle 110, configured to provide power to operate the sound sensor 180.

According to some examples, the communication line 184 is connected, directly or indirectly (e.g., via the internal control unit 194) to a communication component 198 (schematically shown, for example, in FIG. 9). The communication component 198 may be operatively coupled to the control unit 194. The communication component 198 can comprise a transmitter, a receiver, a transceiver, and/or a data communication socket. In some examples, as schematically shown in FIG. 9, communication component $198^b$ is embedded within the handle 110, and may be configured to receive signals from, and/or transmit signals to, components and/or devices external to the delivery assembly 100.

Measurement signals acquired by the at least one sound sensor 180, commensurate with click sounds of the expansion and locking assemblies 138 during valve expansion, may provide real-time feedback regarding the valve expansion diameter during an implantation procedure. Such data may be displayed graphically, for example on an LCD screen 113a or LED lights 113b provided on the handle 110. According to some examples, the control unit 194 is operatively coupled to a display module 196, configured to relay visual representation of the measurement signals, or other signals or data derived from the measurement signals. In some examples, as schematically shown in FIG. 9, display module $196^a$ is configured to relay data or information to be visually displayed via LCD screen 113a or LED lights 113b.

According to some examples, the communication line $184^b$ is attached to the nosecone shaft 108, for example to an outer surface of the nosecone shaft 108, or wrapped therearound, for example in a helical pattern (not shown). According to some examples, communication line 184, such as communication line 1846, extends from the sound sensor 180 (e.g., from sound sensor $180^b$ as illustrated in FIG. 9) to the handle 110, and optionally further extending into the handle 110.

While not illustrated separately, the sound sensor 1800 can be attached to the nosecone 109 and operate in the same manner described hereinabove for any of the examples of the sound sensor $180^b$ attached to the nosecone shaft 108, having the communication line $184^b$ extending therefrom, optionally along a portion of the nosecone 109, and further attached to the nosecone shaft 108, extending from the sound sensor $180^b$ to the handle 110, and optionally further extending into the handle 110.

Figures 10, 11:
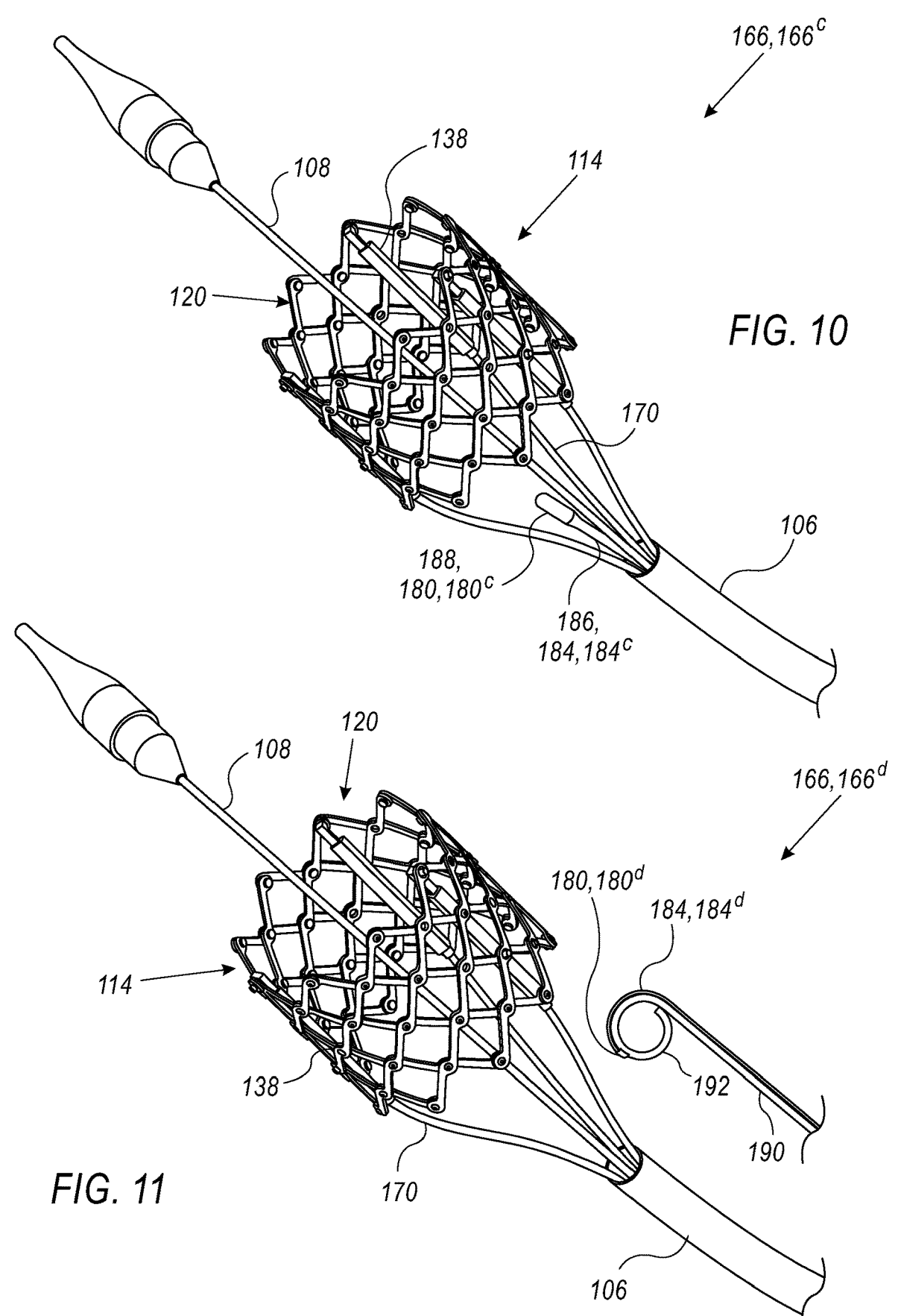
FIG. 10 shows a distal region of the delivery assembly comprising a sensor shaft, according to some examples.
FIG. 11 shows distal region of a prosthetic valve expansion monitoring system comprising a delivery assembly and an independent catheter, according to some examples.

According to some examples, the delivery apparatus 102 further comprises a sensor shaft 186 extending from the handle 110 through the delivery shaft 106. FIG. 10 shows a distal region of the delivery assembly 100 of prosthetic valve expansion monitoring system $166^c$, wherein the sensor shaft 186 comprises a sensing head 188, which is illustrated extending distally from the delivery shaft 106.

The sensor shaft 186 may be axially movable relative to the delivery shaft 106. The movement of the sensor shaft 186 may be controlled by the handle 110. The sensing head 188 may comprise sound sensor $180^c$. The sensor shaft 186 may further comprise communication line $184^c$ extending from the sensing head 188 toward the handle 110.

FIG. 11 shows a distal region of a prosthetic valve expansion monitoring system $166^d$ that comprises, according to some examples, a delivery assembly 100 and an independent catheter 190, which may be similar in structure and function to the sensor shaft 186, except that the independent catheter 190 is provided as a separate component which is not part of the delivery apparatus 102.

The independent catheter 190 may be axially movable relative to any component of the delivery assembly 100. The independent catheter 190 comprises a sensing head 192, which may comprise sound sensor $180^d$. According to some examples, the independent catheter 190 may be provided in the form of a pigtail catheter, as illustrated in FIG. 11.

Sound sensor $180^d$ can be embedded within sensing head 192, or attached to an external surface of sensing head 192 which is a distal end portion of the independent catheter 190. The independent catheter 190 may further comprise communication line $184^d$ extending from the sound sensor 1804, either through a lumen of the independent catheter 190, or over the external surface of the independent catheter 190 as illustrated for example in FIG. 11.

According to some examples, sound sensor 180$^e$ is attached to the delivery shaft 106. In the example of prosthetic valve expansion monitoring system 166$^c$ shown in FIG. 12, the sound sensor 180$^c$ is attached to the outer surface of the delivery shaft 106. Alternatively, the sound sensor 180$^e$ can be attached to the inner surface of the delivery shaft 106.

According to some examples, communication line 184$^e$ is attached to the outer surface of the delivery shaft 106, or wrapped there-around, for example in a helical pattern (not shown), extending from the sound sensor 180$^e$ to the handle 110, and optionally further extending into the handle 110. Alternatively or additionally, the communication line 184$^c$ can be attached to the inner surface of the delivery shaft 106.

While not illustrated separately, the sound sensor 180$^e$ can be attached to any other shaft of the delivery apparatus 102, such as the outer shaft 104, configured to operate in the same manner described hereinabove for any of the examples of the sound sensor 180$^e$ attached to the delivery shaft 106, having the communication line 184$^e$ extending therefrom to the handle 110, and optionally further extending into the handle 110.

Figures 12, 13:
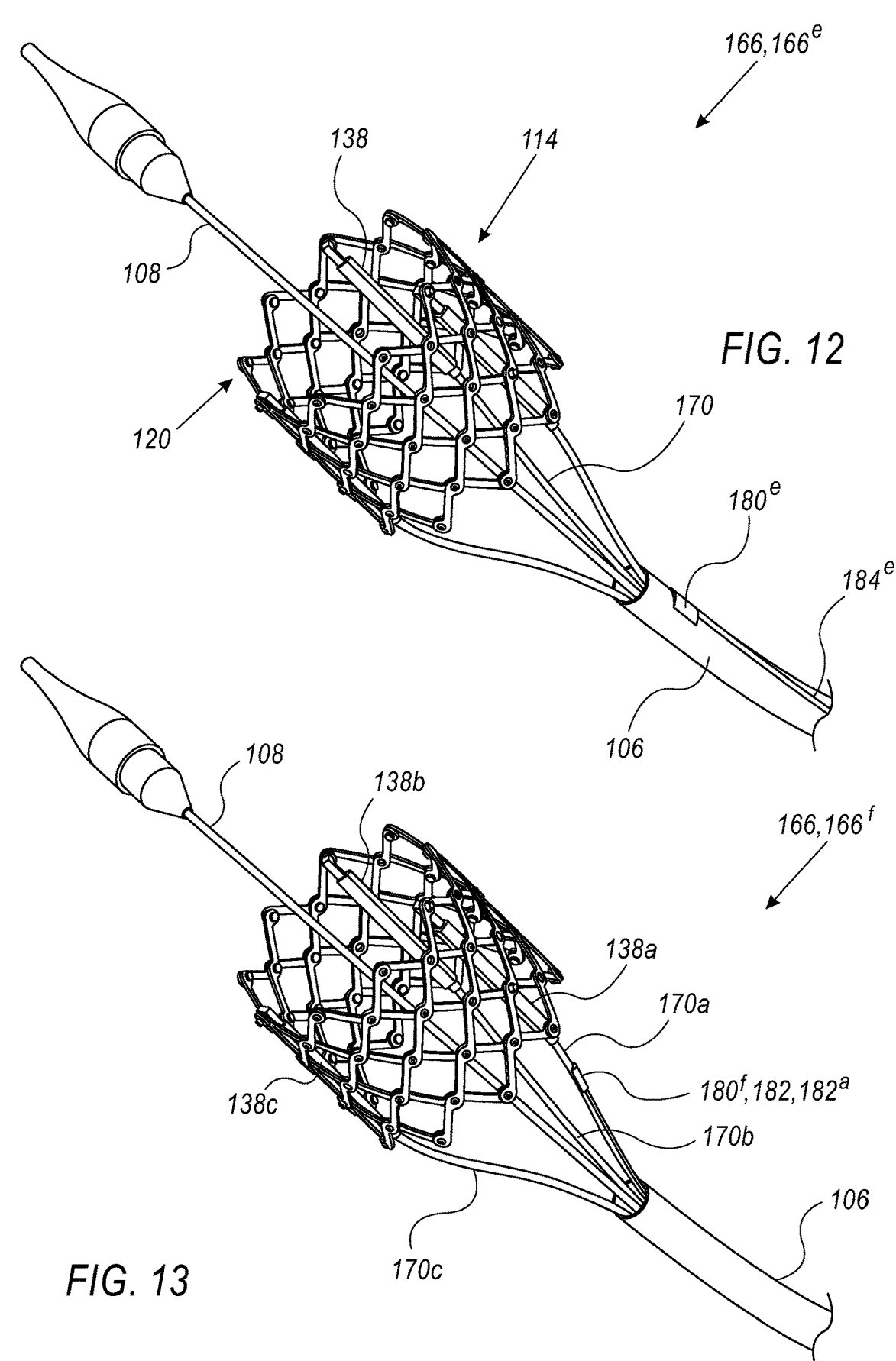
FIG. 12 shows an example of a sound sensor attached to a delivery shaft.
FIG. 13 shows an example of a sound sensor or vibration sensor attached to an actuation assembly.

According to some examples, sound sensor 180$^f$ is attached to a component of an actuation assembly 170. In the example of FIG. 13 the sound sensor 180$^f$ is attached to the outer surface of one of the plurality of actuation assemblies 170. As mentioned, each actuation assembly 170 can include an actuator 172 releasably coupled at its distal end to a respective expansion and locking assembly 138, and a sleeve 176 disposed around the actuator 172. According to some examples, the sound sensor 180$^f$ is attached to the outer surface of a sleeve 176.

According to some examples, communication line 184$^f$ is attached to the outer surface of one of the plurality of actuation assemblies 170, or wrapped there-around, for example in a helical pattern (not shown), from the sound sensor 180$^f$ to the handle 110, and optionally further extending into the handle 110. According to some examples, the communication line 184$^f$ is attached to the outer surface of a sleeve 176.

According to some examples, the delivery apparatus 102 includes a plurality of actuation assemblies, and at least one sound sensor 180$^f$ attached to at least one of the plurality of actuation assemblies. FIG. 13 shows an example of a delivery apparatus 102 that includes three actuation assemblies 170a, 170b and 170c, coupled to three expansion and locking assemblies 138a, 138b and 138c, and a single sound sensor 180$^f$ attached to one of the expansion and locking assemblies, such as to the outer surface of expansion and locking assembly 138a.

It is to be understood that any reference to "the sound sensor" or "the at least one sound sensor" throughout the specification and the claims, refers to each one of the sound sensor in case of configurations that include a plurality of sound sensors.

Figures 14, 15, 16, 17:
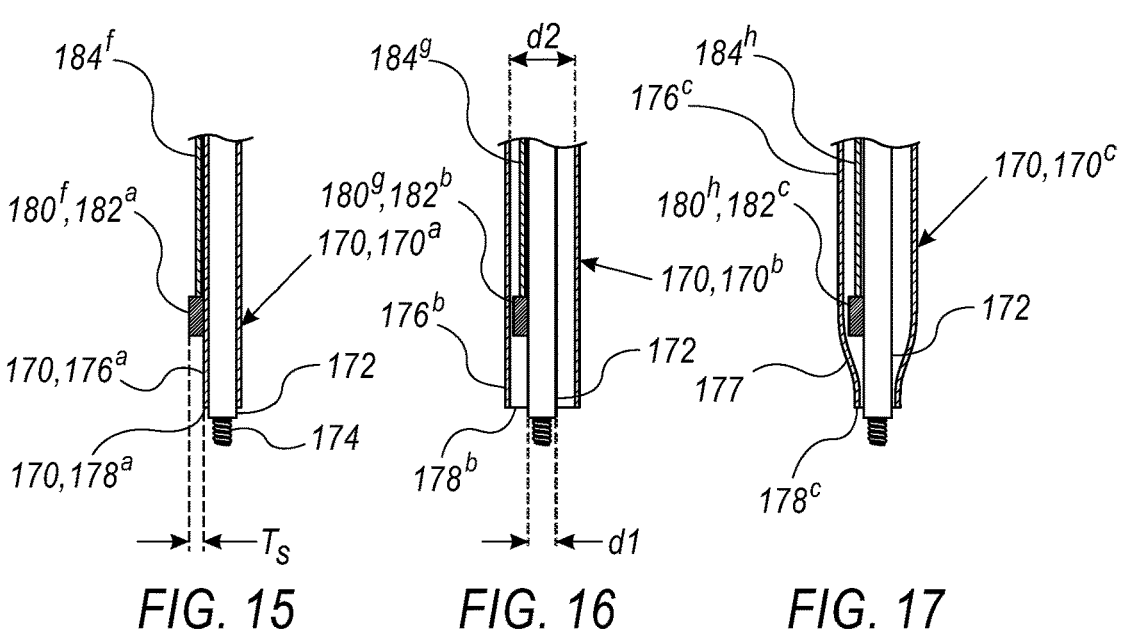
FIG. 14 shows an example of three sound sensors or vibration sensors attached to corresponding actuation assemblies.
FIGS. 15-17 show various configurations of a sound sensor or a vibration sensor attached to a component of an actuation assembly, according to some examples.

According to some examples, the delivery apparatus 102 includes a plurality of sound sensors 180$^f$, attached to a plurality of actuation assemblies 170. The number of sound sensors 180$^f$ can match the number of actuation assemblies 170, which in turn matches the number of expansion and locking assemblies 138. FIG. 14 shows an example of a delivery apparatus 102 that includes three actuation assemblies 170a, 170b and 170c, coupled to three expansion and locking assemblies 138a, 138b and 138c, and three sound sensors 180$^f$a, 180$^f$b and 180$^f$c attached to the actuation assemblies 170a, 170b and 170c, respectively. Three corresponding communication lines 184$^f$a, 184$^f$b and 184$^f$c can extend proximally from the sound sensors 180$^f$a, 180$^f$b and 180$^f$c, respectively.

According to some examples, there is provided a delivery assembly 100 comprising at least one vibration sensor 182 attached to at least one expansion and locking assembly 138, wherein the at least one vibration sensor 182 is configured to detect vibrations of the at least one expansion and locking assembly 138, which are transmitted to the corresponding actuation assembly 170 coupled thereto.

When the pawl 152 slides over each ratcheting tooth 164 of the inner member 154, as described hereinabove with respect to FIGS. 6A-6B, the pawl 152 hits the throughs between consecutive teeth 164 in a manner that is sufficient to vibrate the inner member 154 to some extent. The amplitude of such a vibration may be maximal as the pawl 152 slides over a tooth 164 to hit against the through between the teeth 164, such that each vibration, detected and identified to be indicative of the pawl 152 being slid over a tooth 164, may be indicative of a relative axial movement between the inner member 154 and the outer member 140 along a distance L, which is the length of a single ratcheting tooth 164. The pawl 152 of the outer member 140 may similarly experience a similar vibration from the same reason, though the amplitude and waveform of the vibration wave of the outer member 140 may be different than that of the inner member 154.

Thus, detection of vibration of a component of the expansion and locking assembly 138, such as the inner member 154 and/or the outer member 140, can be indicative of relative axial movement between the inner member 154 and the outer member 140 along a distance L.

The actuation assemblies 170 are releasably coupled to the expansion and locking assemblies 138 during valve expansion procedures, such that vibration of a component of each expansion and locking assembly 138 can be advanced through a component of the respective actuation assembly 170 coupled thereto. For example, since both the inner member 154 and the actuator 170 coupled thereto are rigid components (e.g., metallic components), vibration of the inner member 154 can be axially advanced and cause the actuator 172 to vibrate there-along. The sleeve 176 covering the actuator 172 can also vibrate, either if it is tightly disposed over the actuator 172 in a manner that enables vibrations of the actuator 172 to vibrate the sleeve 176 as well, or due to close contact with the outer member 140 as the distal lip 178 is pushed against the outer member proximal end portion 144.

According to some examples, a vibration sensor 182 can be an accelerometer, or any other type of a biocompatible motion sensor that is biocompatible and configured to detect vibrations generated by components of expansion and locking assemblies 138 transmitted to components of actuation assemblies 170 coupled thereto. The vibration sensor 182, according to any example disclosed herein, is configured to generate electric signals representative of vibrations sensed thereby. Specifically, the vibration sensor 182 is configured to generate signals commensurate with vibrations generated by the corresponding expansion and locking assembly 138 (i.e., the expansion and locking assembly that is releasable coupled to the actuation assembly the vibration sensor is attached to) during movement of the pawl 152 over each ratcheting tooth 164.

Each vibration sensor 182 can be coupled, for example, to a communication line 184, which may take the form of any example of a communication line 184 described hereinabove with respect to the various types of sound sensors, and is configured to transmit the electric signals from the respective vibration sensor 182, and/or deliver power thereto. Similarly, the communication line 184 attached to a vibration sensor 182 on one end thereof, can be coupled to a control unit, as well as to a communication component 198, a power source, and/or a display module 196, according to any of the examples disclosed hereinabove with respect to delivering electric signals from sound sensors 180, mutatis mutandis. The communication line 184 is configured to deliver the electric signals to the control unit 194.

Vibration measurement signals acquired by the at least one vibration sensor 182, commensurate with vibrations of the expansion and locking assemblies 138 during valve expansion, may provide real-time feedback regarding the valve expansion diameter during an implantation procedure. Such data may be displayed graphically, for example on an LCD screen 113a or LED lights 113b provided on the handle 110.

According to some examples, the delivery apparatus 102 includes a plurality of actuation assemblies, and at least one vibration sensor 182 attached to at least one of the plurality of actuation assemblies. FIG. 13 shows an example of a delivery apparatus 102 that includes three actuation assemblies 170a, 170b and 170c, coupled to three expansion and locking assemblies 138a, 138b and 138c, and a single vibration sensor $182^a$ attached to one of the expansion and locking assemblies, such as to the outer surface of expansion and locking assembly 138a. According to some examples, vibration sensor $182^a$ is attached to the outer surface of a sleeve 176, as shown in FIG. 13 or 14.

According to some examples, communication line $184^f$ is attached to the outer surface of a corresponding actuation assembly 170, or wrapped there-around, for example in a helical pattern (not shown), from the vibration sensor $182^a$ to the handle 110, and optionally further extending into the handle 110. According to some examples, the communication line $184^f$ is attached to the outer surface of a sleeve 176.

According to some examples, the delivery apparatus 102 includes a plurality of vibration sensors 182, attached to a plurality of actuation assemblies 170. The number of vibration sensors 182 can match the number of actuation assemblies 170, which in turn matches the number of expansion and locking assemblies 138. FIG. 14 shows an example of a delivery apparatus 102 that includes three actuation assemblies 170a, 170b and 170c, coupled to three expansion and locking assemblies 138a, 138b and 138c, and three vibration sensors $182^a a$, $182^a b$ and $182^a c$ attached to the actuation assemblies 170a, 170b and 170c, respectively. Three corresponding communication lines $184^f a$, $184^f b$ and $184^f c$ can extend proximally from the vibration sensors $182^a a$, $182^a b$ and $182^a c$, respectively.

It is to be understood that any reference to "the vibration sensor" or "the at least one vibration sensor" throughout the specification and the claims, refers to each one of the sound sensor in case of configurations that include a plurality of sound sensors.

Reference is now made to FIGS. 15-17, showing various configurations of a sound sensor 180 or a vibration sensor 182 attached to a component of an actuation assembly 170. FIG. 15 shows an example of a vibration sensor $182^a$ or a sound sensor $180^f$ attached to an external surface of a sleeve 176.

According to some examples, sleeve $176^a$ is tightly disposed around actuator 172, such that vibrations of the actuator 172 are transmitted to the sleeve $176^a$ by contact.

Thus, the inner surface of the sleeve $176^a$ may in contact with the outer surface of the actuator 172. Nevertheless, the sleeve 176 should preferably allow the actuator 172 to be movable axially relative thereto, for example during the pulling of the inner member 154 thereby for valve expansion, with as little interference as possible therebetween. Thus, the sleeve $176^a$ can be tightly disposed around actuator 172 in a manner that a narrow gap is formed therebetween, sufficient to allow free telescoping movement of the actuator 172 with respect to the sleeve $176^a$, yet narrow enough to allow vibrations of the actuator 172 to be transmitted to the sleeve $176^a$.

According to some examples, a lubricious coating may be provided on an outer surface of the actuator 172 and/or the inner surface of the sleeve 176. The lubricious coating can include Teflon, parylene, PTFE, polyethylene, polyvinylidene fluoride, and combinations thereof. Suitable materials for a lubricious coating also include other materials desirably having a coefficient of friction of 0.1 or less. Such coating can allow the sleeve $176^a$ to be tightly disposed around actuator 172 in a manner that will allow vibrations to be transmitted from the actuator 172 to the sleeve $176^a$, so as to be easily sensed by a corresponding vibration sensor $182^a$ attached to the sleeve $176^a$, while allowing the actuator 172 and the sleeve $176^a$ to be conveniently movable relative to each other along the axial axis.

According to some examples, a vibration sensor $182^b$, $182^c$ or a sound sensor $180^g$, $180^h$ is disposed within the lumen defined by the sleeve 176, between the actuator 172 and the sleeve 176. Sleeve $176^b$ can have an inner diameter d2, larger than an outer diameter d1 of the actuator 172. According to some examples, the difference between d2 and d1 is at least twice as large as the thickness Ts of the vibration sensor $182^b$, $182^c$ or the sound sensor $180^g$, $180^h$. According to some examples, the vibration sensor $182^b$, $182^c$ or the sound sensor $180^g$, $180^h$ is attached to the outer surface of the inner member 154, as shown in FIG. 16. Alternatively, the vibration sensor $182^b$, $182^c$ or the sound sensor $180^g$, $180^h$ can be attached to the inner surface of the sleeve $176^b$.

According to some examples, sleeve $176^b$ has a uniform inner diameter d2, as shown in FIG. 16. In other examples, sleeve $176^c$ can have a varying inner diameter, such that the difference between the inner diameter of the sleeve $176^c$ and the outer diameter d1 of the actuator 172 is at least as great as twice the thickness Ts, at least at the region at which the vibration sensor $182^c$ or sound sensor $180^h$ is positioned, and potentially along most of the length of the actuation assembly 170, and include a tapering neck portion 177 distal to vibration sensor $182^c$ or sound sensor $180^h$, as shown in FIG. 17.

The neck portion 177 is tapering from diameter d2 toward the actuator 172 in the distal direction, resulting in the distal lip 178 having a diameter that is narrower than d2, and closer to d1, which may advantageously allow a vibration sensor $182^c$ or sound sensor $180^h$ to be conveniently accommodated between the actuator 172 and the sleeve $176^c$, while the distal lip 178 is dimensioned such that it may contact the outer member proximal end portion 144 and provide a counter-force there-against during valve expansion, as described hereinabove with respect to FIGS. 7A-7C.

According to some examples, communication line $184^g$, $184^h$ is disposed within the lumen defined by the sleeve 176, between the actuator 172 and the sleeve 176, extending proximally from the vibration sensor $182^b$, $182^c$ or the sound sensor $180^g$, $180^h$ to the handle 110, and optionally further extending into the handle 110. Communication line $184^g$, $184^h$ can be attached to the outer surface of the actuator 172, or wrapped there-around, for example in a helical pattern (not shown). Alternatively, communication line $184^g$, $184^h$ can be attached to the inner surface of sleeve $176^b$, $176^c$.

While illustrated in the examples to be positioned in the vicinity of the prosthetic valve 114, for example along a distal portion of the actuation assembly 170, it is to be understood that in alternative implementations, the vibration sensors 182 can be attached to other portions of the actuation assemblies 170. For example, vibration sensors 182 can be attached to proximal portions of the actuation assemblies 170, including configurations of vibration sensors 182 attached to proximal portions of the actuators 172 situated within the handle 110. Such configurations may be feasible is the actuators 172 are provided with rigidity that is sufficient to transmit vibrations from the inner members 154 coupled thereto all the way to their proximal portions (e.g., within the handle) in a manner that is sufficient to detect vibrations commensurate with the pawls 152 sliding over respective ratcheting teeth 164.

Ambient sounds and noise may be present during the implantation and expansion procedure, including heart sounds, lung sounds, blood flow in the vicinity of the prosthetic valve 114 and/or the sound sensor 180, movement of various components such as the leaflets 133 of the leaflet assembly 132 that may move between open and closed states as the valve is expanded enough to allow blood flow therethrough, and the like. According to some examples, the control unit 194 is configured to filter ambient sounds and/or noise, so as to detect and isolate click sounds generated by the expansion and locking assemblies 138.

The amplitude, waveform and frequency of click sounds, generated by the interaction of potentially metallic components, such as the pawl 152 and the ratcheting teeth 164, may be distinguishable from that of other ambient sounds and/or noise. Moreover, some ambient sounds may be periodically repeating sounds, related to ongoing repetitive physiological function of the tissues generating such sounds, while the click sounds are discretely generated only during valve expansion.

According to some examples, the control unit 194 comprises a processor for processing and interpreting measurement signals received from the at least one sound sensor 180 and/or the at least one vibration sensor 182. The control unit 194 may include software for interpreting and/or displaying data. A wide variety of algorithms can be used to provide warnings, for example to the clinician, associated with sensed signals interpretations. Thus, an operator of the delivery assembly 100 according to any of the examples of the current disclosure, can quickly and easily obtain real-time assessment of the expanded diameter of the prosthetic valve 114.

According to some examples, the control unit 194 further comprises a memory member (not shown), such as an internal memory within the control unit 194, configured to store the signals received from any of the sound sensor 180 and/or the vibration sensor 182, and/or store interpreted data by the processor. A memory member may include a suitable memory chip or storage medium such as, for example, a PROM, EPROM, EEPROM, ROM, flash memory, solid state memory, or the like. A memory member can be integral with the control unit or may be removably coupled to the control unit.

The terms "signals", "electric signals", and "measurement signals", as used herein, are interchangeable.

According to some examples, the measurement signals may be mathematically manipulated or processed by the control unit 194, in order to derive axial foreshortening and/or valve expansion diameter.

According to some examples, the internal control unit 194 is configured to transmit, for example via the communication component 198, raw or interpreted data, including stored data, to an external control unit or any other external device, via either wired or wireless communication protocols.

According to some examples, the control unit 194 can be configured to receive electric signals detected by the at least one sound sensor 180, and to filter signals that may follow amplitudes, waveforms and/or frequencies that may be associated with ambient sounds and/or noise, leaving only the signals that may follow amplitudes, waveforms and/or frequencies that may be associated with click sounds.

According to some examples, the control unit 194 be configured to receive electric signals detected by the at least one sound sensor 180, and to filter signals that are present prior to initiation of valve expansion. According to some examples, the control unit 194 may be associated with the actuation mechanism within the handle 110 that is configured to pull the actuators 172, such that an expansion initiation signal is generated at the onset of pulling the actuators 172, and is sent to the control unit 194, allowing the control unit to filter signals sensed by the at least one sound sensor 180 prior to the onset of pulling the actuators 172.

According to some examples, the control unit 194 is further configured to detect and count the number of click sounds. According to some examples, the axial foreshortening of the prosthetic valve 114, defined as the axial approximation of the inflow end 119 and the outflow end 117 toward each other during valve expansion, can be estimated by multiplying the number of detected clicks by the axial length of a ratcheting tooth L. For example, a count of a total of 5 clicks can be indicative of a valve foreshortening by a distance of about 5 L.

Assuming that the relationship between axial foreshortening and radial expansion is known for the specific valve type, the radial expansion can then be derived from the estimated axial foreshortening. Assuming that the diameter of the prosthetic valve 114 at which the pawl 152 is engaged with the first ratcheting tooth 164 to generate the first click sound is known, this initial diameter can serve as the base value to which the additional expansion diameter is added.

Thus, based on the assumptions of such pore-stored known relationships, the at least one sound sensor 180 may be utilized to provide an indication, qualitative or quantitative evaluation, or any other feedback regarding the expanded diameter of prosthetic valve 114, in real-time, in-vivo, during a valve 114 implantation and expansion procedures.

Since the click sounds are generated at discrete points, once the pawl 152 slides over a tooth 164 having a length L, the estimated diameter may have an accuracy in the range of L.

The prosthetic valve 114 may include a plurality of expansion and locking assemblies 138, such as three expansion and locking assemblies 138a, 138b and 138c in the illustrated examples. In some cases, the distance by which the inner member 154 moves relative to the corresponding outer member 140 in each of the expansion and locking assemblies 138 may slightly differ from each other, and the click sounds generated by each may not necessarily be synchronized with each other.

According to some examples, the control unit is further configured to differentiate between click sounds of different expansion and locking assemblies based on identification of the time difference between such click sounds. For example, unsynchronized click sounds generated by different expansion and locking assemblies, detected at time intervals that are shorter than a predefined threshold, may be indicative of click sounds of two or more expansion and locking assemblies 138 actuated simultaneously, while time intervals that are longer than the predefined threshold may be indicative of the pawl of at least one expansion and locking assembly 138 sliding over a subsequent tooth 164.

The maximal difference between non-simultaneously moving inner members 154 may be in the range of L or 2 L, and may thus influence the accuracy of diameter estimation, which can be, for example, in the range of a foreshortening of L or 2 L, respectively. For example, if the length of a single ratcheting tooth L is about 0.2 mm., an extreme situation in which all three expansion and locking assemblies 138 move asynchronously and may generate three consecutive click sounds that actually represent a valve foreshortening of no more than a length of single tooth, a foreshortening of 3 L, i.e., of about 0.6 mm., might be assumed instead of an actual foreshortening of L, i.e. of about 0.2 mm., resulting in an error range of about 2 L (i.e., 4 mm.) between the estimated and actual foreshortening. Thus, the length L of ratcheting teeth 164 may influence the accuracy of diameter estimation, based on counting click sounds detected by the at least one sound sensor 180.

The relation between axial foreshortening of the valve and diameter expansion can be a non-linear relation, wherein the diameter of the valve can be increased by a value that is either shorter than, equal to, or larger than the axial foreshortening. The accuracy of estimating valve axial foreshortening may influence the accuracy of estimating the expansion diameter based on such relation. For example, a foreshortening of about 0.4 mm. in a maximal or near maximal expansion diameter of the valve may be translated to an increase in diameter of about 0.5 mm., such that an error range of about 2 L of the estimated foreshortening may result in an error range of about 2.5 L of the estimated expansion diameter. While the accuracy of axial foreshortening may be equal along the range of valve foreshortening values, the accuracy of the expansion diameter derived therefrom may change at different diameters for cases in which the relation between axial foreshortening and radial expansion is non-linear.

The ratcheting tooth length L may be selected to provide sufficient accuracy to the estimated axial foreshortening and the expansion diameter derives therefrom. A smaller tooth length L will increase the accuracy of the estimated values and the resolution of intermediate expansion diameters that may be estimated and presented to a user of the delivery assembly 100.

Utilization of vibration sensors 182 may be advantageous over sound sensors 180 in that vibration sensors 182 can be less influenced by ambient sounds and noise. Nevertheless, some ambient sounds and movement of tissues in the vicinity of the prosthetic valve 114, as well as movement of components of the delivery apparatus 102 and/or the prosthetic valve 114, may create background vibrations that may be detected by the vibration sensors 182. According to some examples, the control unit 194 is configured to filter background vibrations, so as to detect and isolate vibrations generated by the expansion and locking assemblies 138 during movement of the pawl 152 over each tooth 164.

The amplitude, waveform and frequency of vibrations generated by the expansion and locking assemblies 138 during movement of the pawl 152 over each tooth 164, may be distinguishable from that of background vibrations.

According to some examples, the control unit 194 can be configured to receive electric signals detected by the at least one vibration sensor 182, and to filter signals that may follow amplitudes, waveforms and/or frequencies that may be associated with background vibrations, leaving only the signals that may follow amplitudes, waveforms and/or frequencies that may be associated with vibrations generated by the expansion and locking assemblies 138 during movement of the pawl 152 over each tooth 164.

According to some examples, the control unit 194 be configured to receive electric signals detected by the at least one vibration sensor 182, and to filter signals that are present prior to initiation of valve expansion. According to some examples, the control unit 194 may be associated with the actuation mechanism within the handle 110 that is configured to pull the actuators 172, such that an expansion initiation signal is generated at the onset of pulling the actuators 172, and is sent to the control unit 194, allowing the control unit to filter signals sensed by the at least one vibration sensor 182 prior to the onset of pulling the actuators 172.

According to some examples, the control unit 194 is further configured to detect and count the number of vibrations generated by the expansion and locking assemblies 138 during movement of the pawl 152 over each tooth 164. The axial foreshortening, the derivation of the valve expanded diameter therefrom, and the accuracy of such estimations, may be similar to those described above with respect to the counted click sounds, mutatis mutandis.

Utilization of vibration sensor 182 may be advantageous over that of sound sensors 180, as a plurality of vibration sensors 182 can be coupled to a corresponding plurality of actuation assemblies 170, as shown for example in FIG. 14, allowing the axial movement of each inner member 154 relative to a respective outer member 140 of each expansion and locking assembly 138 to be measured separately by a corresponding different vibration sensor 182. The signals from the plurality of vibration sensors 182 can then be transmitted to the control unit 194, which can in turn mathematically manipulate signals acquired within a predefined time period that may be associated with signals that may originate from different expansion and locking assemblies 138 but relate to the same range of frame foreshortening. Such mathematical manipulation can include for example averaging the axial translations of the plurality of expansion and locking assemblies 138, so as to improve the accuracy of the valve expanded diameter derived therefrom.

According to some examples, signals from vibration sensors 182 attached to different actuation assemblies 170, each indicative of the axial foreshortening of a separate expansion and locking assembly 138, serve to identify non-uniform expansion of the prosthetic valve 114, and to estimate the extent of such non-uniformity that can be displayed to the operator (e.g., clinician) of the delivery assembly 100. Information regarding non-uniformity of valve expansion, that can include data regarding the extent of foreshortening along different regions of the circumference of the prosthetic valve 114, and potentially the resulting, potentially non-circular circumferential contour of valve expansion, may be of high significance and is not easily detectable by a sound sensor 180, as well as by other conventional (e.g., image based) assessments of the expansion diameter of the valve. Such data can be displayed (e.g., via display module 196 relaying display data to a display 112) either as textual data that includes numerical values of the various magnitudes of axial foreshortening and locations thereof across the prosthetic valve, as well as graphical representation of such regions and an estimated shape (e.g., non-circular shape) of the expanded prosthetic valve.

ADDITIONAL EXAMPLES OF THE DISCLOSED TECHNOLOGY

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A prosthetic valve expansion monitoring system, comprising: a prosthetic valve comprising: a frame movable between a radially compressed configuration and a radially expanded configuration, and at least one expansion and locking assembly, comprising: an outer member, coupled to the frame at a first location, and comprising a spring biased arm with a pawl; and an inner member, coupled to the frame at a second location spaced apart from the first location, the inner member extending at least partially into the outer member, the inner member comprising a plurality of ratcheting teeth; a delivery apparatus comprising: a handle; a delivery shaft extending distally from the handle; and at least one actuation assembly, comprising: an actuator extending from the handle through the delivery shaft, and releasably coupled to the corresponding inner member; and a sleeve disposed around the corresponding actuator, at least one sound sensor configured to generate signals commensurate with click sounds generated during movement of the pawl over the ratcheting teeth; wherein the spring biased arm is biased toward the inner member; and wherein engagement of the pawl with the ratcheting teeth allows movement in a first direction to allow axial foreshortening and radial expansion of the frame and prevents movement in a second direction to prevent radial compression of the frame.

Example 2. The system of any example herein, particularly example 1, wherein the at least one sound sensor is comprised within a sensor housing.

Example 3. The system of any example herein, particularly example 1 or 2, further comprising a control unit configured to: receive the signals from the at least one sound sensor; responsive to the received signals, determine the number of click sounds generated during the movement of the pawl; evaluate an expanded diameter of the prosthetic valve; and output an indication of the evaluated expanded diameter.

Example 4. The system of any example herein, particularly example 3, wherein the control unit is further configured to estimate the axial foreshortening of the frame by multiplying the number of click sounds by the length of a single ratcheting tooth, the evaluation of the expanded diameter being responsive to the estimated axial foreshortening.

Example 5. The system of any example herein, particularly example 4, wherein the evaluation of the expanded diameter is based on pre-stored relationships between axial foreshortening and radial expansion of the frame.

Example 6. The method of any example herein, particularly any one of examples 3 to 5, wherein the at least one expansion and locking assembly comprises three expansion and locking assemblies, and wherein the control unit is further configured to differentiate between click sounds of different expansion and locking assemblies based on identification of the time difference between such click sounds.

Example 7. The system of any example herein, particularly any one of examples to 6, wherein the control unit is embedded within the handle.

Example 8. The system of any example herein, particularly any one of examples 3 to 7, further comprising a communication component operatively coupled to the control unit.

Example 9. The system of any example herein, particularly example 8, wherein the communication component is embedded within the handle.

Example 10. The system of any example herein, particularly any one of examples 3 to 9, further comprising a display module operatively coupled to the control unit.

Example 11. The system of any example herein, particularly example 10, wherein the handle further comprises an LCD screen and/or LED lights, and wherein the display module is configured to relay visual representation of the signals, or data derived from the signals, to the LCD screen and/or the LED lights.

Example 12. The system of any example herein, particularly any one of examples 1 to 11, further comprising at least one communication line attached to the at least one sound sensor, and configured to transmit signals generated by the sound sensor.

Example 13. The system of any example herein, particularly example 12, wherein the at least one communication line extends from the sound sensor toward and into the handle.

Example 14. The system of any example herein, particularly example 12 or 13, wherein the communication line is further configured to deliver power to the sound sensor.

Example 15. The system of any example herein, particularly any one of examples 1 to 14, wherein the sound sensor comprises a microphone.

Example 16. The system of any example herein, particularly example 15, wherein the microphone is selected from a piezoelectric, a piezoresistive, and a capacitive-type microphone.

Example 17. The system of any example herein, particularly example 15, wherein the microphone is a MEMS microphone.

Example 18. The system of any example herein, particularly any one of examples 1 to 17, wherein the distance between the sound sensor and the pawl is not greater than 20 centimeters.

Example 19. The system of any example herein, particularly example 18, wherein the distance between the sound sensor and the pawl is not greater than 10 centimeters.

Example 20. The system of any example herein, particularly example 19, wherein the distance between the sound sensor and the pawl is not greater than 5 centimeters.

Example 21. The system of any example herein, particularly any one of examples 1 to 20, wherein the sound sensor is attached to the delivery apparatus.

Example 22. The system of any example herein, particularly example 21, wherein the delivery apparatus further comprises a nosecone shaft extending distally from the handle through the delivery shaft, and a nosecone attached to a distal end of the nosecone shaft.

Example 23. The system of any example herein, particularly example 22, wherein the sound sensor is attached to the nosecone shaft.

Example 24. The system of any example herein, particularly example 22, wherein the sound sensor is attached to the nosecone.

Example 25. The system of any example herein, particularly example 21, wherein the delivery apparatus further comprises a sensor shaft extending from the handle through the delivery shaft, wherein the sensor shaft comprises a sensing head comprising the sound sensor.

Example 26. The system of any example herein, particularly example 21, wherein the sound sensor is attached to the delivery shaft.

Example 27. The system of any example herein, particularly example 21, wherein the delivery apparatus further comprises an outer shaft disposed around the delivery shaft, and wherein the sound sensor is attached to the outer shaft.

Example 28. The system of any example herein, particularly example 27, wherein the at least one sound sensor is attached to the at least one actuation assembly.

Example 29. The system of any example herein, particularly example 28, wherein the at least one sound sensor comprises a single sound sensor attached to one of the actuation assemblies.

Example 30. The system of any example herein, particularly example 28, wherein the at least one sound sensor comprises three sound sensors, each attached to a separate actuation assembly.

Example 31. The system of any example herein, particularly any one of examples 28 to 30, wherein the sound sensor is attached to the sleeve.

Example 32. The system of any example herein, particularly any one of examples 28 to 30, wherein the sound sensor is disposed between the actuator and the sleeve.

Example 33. The system of any example herein, particularly example 32, wherein the sound sensor is attached to the actuator.

Example 34. The system of any example herein, particularly example 32 or 33, wherein the difference between an inner diameter of the sleeve and an outer diameter of the actuator is at least twice as large as the thickness of the sound sensor.

Example 35. The system of any example herein, particularly example 32 or 33, wherein the sleeve has a non-uniform inner diameter such that the difference between the inner diameter of the sleeve and an outer diameter of the actuator is at least twice as large as the thickness of the sound sensor at the region at which the sound sensor is positioned, and wherein the sleeve comprises a neck portion tapering distally inward to a narrower inner diameter of the sleeve.

Example 36. The system of any example herein, particularly any one of examples 1 to 20, further comprising an independent catheter that is not attached to the delivery apparatus, wherein the independent catheter comprises a sensing head comprising the sound sensor.

Example 37. The system of any example herein, particularly example 36, wherein the independent catheter is a pigtail catheter.

Example 38. The system of any example herein, particularly any one of examples 1 to 20, wherein the sound sensor is an extracorporeal sound sensor, configured to externally measure sounds produced within the body of a subject.

Example 39. The system of any example herein, particularly example 38, wherein the extracorporeal sound sensor is embedded within a precordial patch.

Example 40. The system of any example herein, particularly example 38 or 39, wherein the extracorporeal sound sensor is further configured to detect heart sounds.

Example 41. The system of any example herein, particularly any one of examples 38 to 40, wherein the extracorporeal sound sensor is a phonocardiogram sensor.

Example 42. A delivery assembly, comprising: a prosthetic valve comprising: a frame movable between a radially compressed configuration and a radially expanded configuration, and at least one expansion and locking assembly, comprising: an outer member, coupled to the frame at a first location, and comprising a spring biased arm with a pawl; and an inner member, coupled to the frame at a second location spaced apart from the first location, the inner member extending at least partially into the outer member, the inner member comprising a plurality of ratcheting teeth; a delivery apparatus comprising: a handle; a delivery shaft extending distally from the handle; and at least one actuation assembly, comprising: an actuator extending from the handle through the delivery shaft, and releasably coupled to the corresponding inner member; and a sleeve disposed around the corresponding actuator, at least one vibration sensor attached to the at least one actuation assembly; wherein the spring biased arm is biased toward the inner member; wherein engagement of the pawl with the ratcheting teeth allows movement in a first direction to allow axial foreshortening and radial expansion of the frame and prevents movement in a second direction to prevent radial compression of the frame; and wherein the vibration sensor is configured to generate signals commensurate with vibrations generated by the expansion and locking assembly during movement of the pawl over each ratcheting tooth.

Example 43. The delivery assembly of any example herein, particularly example 42, further comprising a control unit configured to: receive the signals from the at least one vibration sensor; responsive to the received signals, count the vibrations generated by the expansion and locking assembly during movement of the pawl over each ratcheting tooth; responsive to an outcome of the count of the vibrations, evaluate an expanded diameter of the prosthetic valve; and output an indication of the expanded diameter.

Example 44. The delivery assembly of any example herein, particularly example 43, wherein the control unit is further configured to estimate the axial foreshortening of the frame by multiplying the number of vibrations generated by the expansion and locking assembly during movement of the pawl over each ratcheting tooth, by the length of a single ratcheting tooth, the evaluation of the expanded diameter responsive to the estimated axial foreshortening.

Example 45. The delivery assembly of any example herein, particularly example 44, wherein the evaluation of the expanded diameter of the prosthetic valve is based on pre-stored relationships between axial foreshortening and radial expansion of the frame.

Example 46. The delivery assembly of any example herein, particularly any one of examples 43 to 45, wherein the at least expansion and locking assembly comprises three expansion and locking assemblies, wherein the at least one vibrations sensor comprises three vibration sensors, each vibration sensor attached to a separate actuation assembly coupled to a corresponding expansion and locking assembly, and wherein the control unit is further configured to identify signals acquired within a predefined time period and mathematically manipulate such signals.

Example 47. The delivery assembly of any example herein, particularly example 46, wherein the mathematical manipulation comprises averaging the signals received within the predefined time period.

Example 48. The delivery assembly of any example herein, particularly example 46 or 47, wherein the control unit is further configured to identify a non-uniform expansion of the prosthetic valve, the evaluation of the expanded diameter responsive to the identified non-uniform expansion.

Example 49. The delivery assembly of any example herein, particularly example 48, wherein the identification of a non-uniform expansion comprises estimating the extent of axial foreshortening at more than two regions around the circumference of the prosthetic valve.

Example 50. The delivery assembly of any example herein, particularly example 49, wherein the identification of a non-uniform expansion comprises estimating the circumferential contour of the expanded prosthetic valve.

Example 51. The delivery assembly of any example herein, particularly any one of examples 43 to 50, wherein the control unit is embedded within the handle.

Example 52. The delivery assembly of any example herein, particularly any one of examples 43 to 51, further comprising a communication component operatively coupled to the control unit.

Example 53. The delivery assembly of any example herein, particularly example 52, wherein the communication component is embedded within the handle.

Example 54. The delivery assembly of any example herein, particularly any one of examples 43 to 53, further comprising a display module operatively coupled to the control unit.

Example 57. The delivery assembly of any example herein, particularly example 56, wherein the handle further comprises an LCD screen and/or LED lights, and wherein the display module is configured to relay visual representation of the signals, or data derived from the signals, to the LCD screen and/or the LED lights.

Example 58. The delivery assembly of any example herein, particularly any one of examples 42 to 57, further comprising at least one communication line attached to the at least one vibration sensor, and configured to transmit signals detected by the vibration sensor.

Example 59. The delivery assembly of any example herein, particularly example 58, wherein the at least one communication line extends from the vibration sensor toward and into the handle.

Example 60. The delivery assembly of any example herein, particularly example 58 or 59, wherein the communication line is further configured to deliver power to the vibration sensor.

Example 61. The delivery assembly of any example herein, particularly any one of examples 42 to 60, wherein the vibration sensor comprises an accelerometer.

Example 62. The delivery assembly of any example herein, particularly example 61, wherein the at least one vibration sensor comprises a single vibration sensor attached to one of the actuation assemblies.

Example 63. The delivery assembly of any example herein, particularly example 61, wherein the at least one vibration sensor comprises three vibration sensors, each attached to a separate actuation assembly.

Example 64. The delivery assembly of any example herein, particularly any one of examples 42 to 63, wherein the vibration sensor is attached to the sleeve.

Example 65. The delivery assembly of any example herein, particularly example 64, wherein the sleeve is tightly disposed around the corresponding actuator.

Example 66. The delivery assembly of any example herein, particularly example 64 or 65, wherein the actuation assembly further comprises a lubricious coating provided on an outer surface of the actuator and/or the inner surface of the sleeve.

Example 67. The delivery assembly of any example herein, particularly example 66, wherein the lubricious coating comprises any of: Teflon, parylene, PTFE, polyethylene, polyvinylidene fluoride, and combinations thereof.

Example 68. The delivery assembly of any example herein, particularly example 66 or 67, wherein the lubricious coating has a coefficient of friction of 0.1 or less.

Example 69. The delivery assembly of any example herein, particularly any one of examples 42 to 68, wherein the vibration sensor is disposed between the actuator and the sleeve.

Example 70. The delivery assembly of any example herein, particularly example 69 wherein the vibration sensor is attached to the actuator.

Example 71. The delivery assembly of any example herein, particularly example 69 or 70, wherein the difference between an inner diameter of the sleeve and an outer diameter of the actuator is at least twice as large as the thickness of the vibration sensor.

Example 72. The delivery assembly of any example herein, particularly example 69 or 70, wherein the sleeve has a non-uniform inner diameter such that the difference between the inner diameter of the sleeve and an outer diameter of the actuator is at least twice as large as the thickness of the vibration sensor at the region at which the vibration sensor is positioned, and wherein the sleeve comprises a neck portion tapering distally inward to a narrower inner diameter of the sleeve.

Example 73. A method of estimating the expanded diameter of a prosthetic valve, comprising: providing a prosthetic valve comprising a frame movable between a radially compressed configuration and a radially expanded configuration, and at least one expansion and locking assembly comprising an outer member coupled to the frame at a first location and comprising a spring biased arm with a pawl, and an inner member, coupled to the frame at a second location spaced apart from the first location and comprising a plurality of ratcheting teeth, wherein the spring biased arm is biased toward the inner member; pulling the inner member relative to the outer member, wherein engagement of the pawl with the ratcheting teeth facilitates axial foreshortening and radial expansion of the frame; generating, by at least one sound sensor, signals commensurate with click sounds generated during movement of the pawl over the ratcheting teeth; evaluating, based on the number of detected click sounds, the expanded diameter of the prosthetic valve; and outputting an indication of the evaluated expanded diameter.

Example 74. The method of any example herein, particularly example 73, wherein the sound sensor is attached to a delivery apparatus that comprises a handle, a delivery shaft extending distally from the handle, a nosecone shaft with a nosecone attached to a distal end thereof, and at least one actuation assembly comprising an actuator extending from the handle and releasably coupled to the corresponding inner member, and a sleeve disposed around the corresponding actuator.

Example 75. The method of any example herein, particularly example 74, wherein the sound sensor is attached to the nosecone shaft.

Example 76. The method of any example herein, particularly example 74, wherein the sound sensor is attached to the nosecone.

Example 77. The method of any example herein, particularly example 74, wherein the sound sensor is attached to the delivery shaft.

Example 78. The method of any example herein, particularly example 74, wherein the sound sensor is attached to the actuation assembly.

Example 79. The method of any example herein, particularly example 78, wherein the sound sensor is attached to the sleeve.

Example 80. The method of any example herein, particularly example 74, wherein the evaluation of the expanded diameter is performed by a control unit embedded within the handle.

Example 81. The method of any example herein, particularly any one of examples 74 to 80, further comprising a step of filtering signals that may follow amplitudes, waveforms and/or frequencies that may be associated with ambient sounds and/or noise, leaving only the signals that may follow amplitudes, waveforms and/or frequencies that may be associated with click sounds.

Example 82. The method of any example herein, particularly example 81, wherein the handle comprises an actuation mechanism configured to pull the actuators, wherein the method further comprises generating an initiation signal at the onset of pulling the actuators by the actuation mechanism, and wherein the filtering of signals associated with ambient sounds and/or noise comprises filtering signals sensed by the at least one sound sensor prior to the initiation signal.

Example 83. The method of any example herein, particularly any one of examples 73 to 82, further comprising a step of detecting and counting click sounds, the evaluation of the expanded diameter being responsive to an outcome of the counting.

Example 84. The method of any example herein, particularly example 83, further comprising a step of estimating the axial foreshortening of the frame by multiplying the number of click sounds by the length of a single ratcheting tooth, the evaluation being responsive to the estimated axial foreshortening.

Example 85. The method of any example herein, particularly example 84, wherein the evaluation of the expanded diameter of the prosthetic valve is based on pre-stored relationships between axial foreshortening and radial expansion of the frame.

Example 86. The method of any example herein, particularly any one of examples 83 to 85, wherein the prosthetic valve comprises three expansion and locking assemblies, and wherein the method further comprises differentiating between click sounds of different expansion and locking assemblies based on identification of the time difference between such click sounds, the evaluation of the expanded diameter being responsive to the difference between the click sounds.

Example 87. A method of estimating the expanded diameter of a prosthetic valve, comprising: providing a prosthetic valve comprising a frame movable between a radially compressed configuration and a radially expanded configuration, and at least one expansion and locking assembly comprising an outer member coupled to the frame at a first location and comprising a spring biased arm with a pawl, and an inner member, coupled to the frame at a second location spaced apart from the first location and comprising a plurality of ratcheting teeth, wherein the spring biased arm is biased toward the inner member; pulling the inner member relative to the outer member, wherein engagement of the pawl with the ratcheting teeth facilitates axial foreshortening and radial expansion of the frame; generating, by at least one vibration sensor, signals commensurate with vibrations generated by the expansion and locking assembly during movement of the pawl over each ratcheting tooth; and evaluating, based on the number of detected vibrations generated during movement of the pawl over each ratcheting tooth, the expanded diameter of the prosthetic valve.

Example 88. The method of any example herein, particularly example 87, wherein the vibration sensor is attached to at least one actuation assembly comprising an actuator extending from a handle and releasably coupled to the corresponding inner member, and a sleeve disposed around the corresponding actuator.

Example 89. The method of any example herein, particularly example 88, wherein the vibration sensor is attached to the sleeve.

Example 90. The method of any example herein, particularly example 89, wherein the vibration sensor is attached to the actuator.

Example 91. The method of example 89, wherein the evaluation of the expansion diameter is performed by a control unit embedded within the handle.

Example 92. The method of any one of examples 87 to 91, further comprising the step of filtering signals that may follow amplitudes, waveforms and/or frequencies that may be associated with ambient background vibrations, leaving only the signals that may follow amplitudes, waveforms and/or frequencies that may be associated with vibrations generated by the expansion and locking assembly during movement of the pawl over each ratcheting tooth.

Example 93. The method of any example herein, particularly example 92, wherein the handle comprises an actuation mechanism configured to pull the actuators, wherein the method further comprises generating an initiation signal at the onset of pulling the actuators by the actuation mechanism and sending the initiation signal to the control unit, and wherein the filtering of signals associated with background vibrations comprises filtering signals sensed by the at least one vibrations sensor prior to the initiation signal.

Example 94. The method of any example herein, particularly any one of examples 87 to 93, further comprising the step of detecting and counting the vibrations generated by the expansion and locking assembly during movement of the pawl over each ratcheting tooth, the evaluation of the expanded diameter being responsive to an outcome of the counting of the vibrations.

Example 95. The method of any example herein, particularly example 94, further comprising a step of estimating the axial foreshortening of the frame by multiplying the number of vibrations generated by the expansion and locking assembly during movement of the pawl over each ratcheting tooth, by the length of a single ratcheting tooth, the evaluation of the expanded diameter being responsive to the estimation of the axial foreshortening.

Example 96. The method of any example herein, particularly example 95, wherein the evaluation of the expanded diameter of the prosthetic valve is based on pre-stored relationships between axial foreshortening and radial expansion of the frame.

Example 97. The method of any example herein, particularly any one of examples 94 to 96, wherein the prosthetic valve comprises three expansion and locking assemblies, wherein the at least one vibrations sensor comprises three vibration sensors, each vibration sensor attached to a separate actuation assembly coupled to a corresponding expansion and locking assembly, and wherein the method further comprises identifying signals acquired within a predefined time period and mathematically manipulating such signals.

Example 98. The method any example herein, particularly example 97, wherein the mathematical manipulation comprises averaging the signals received within the predefined time period.

Example 99. The method of any example herein, particularly example 97 or 98, wherein the method further comprises identifying a non-uniform expansion of the prosthetic valve, the evaluation of the expansion diameter responsive to the identified non-uniform expansion.

Example 100. The method of any example herein, particularly example 99, wherein the step of identifying a non-uniform expansion further comprises estimating the extent of axial foreshortening at more than two regions around the circumference of the prosthetic valve.

Example 101. The method of any example herein, particularly example 100, wherein the step of identifying a non-uniform expansion further comprises estimating the circumferential contour of the expanded prosthetic valve.

It is appreciated that certain features of the invention, which are, for clarity, described in the context of separate examples, may also be provided in combination in a single example. Conversely, various features of the invention, which are, for brevity, described in the context of a single example, may also be provided separately or in any suitable sub-combination or as suitable in any other described example of the invention. No feature described in the context of an example is to be considered an essential feature of that example, unless explicitly specified as such.

Although the invention is described in conjunction with specific examples thereof, it is evident that numerous alternatives, modifications and variations that are apparent to those skilled in the art may exist. It is to be understood that the invention is not necessarily limited in its application to the details of construction and the arrangement of the components and/or methods set forth herein. Other examples may be practiced, and an example may be carried out in various ways. Accordingly, the invention embraces all such alternatives, modifications and variations that fall within the scope of the appended claims.

The invention claimed is:

1. A prosthetic valve expansion monitoring system, comprising:
  a prosthetic valve comprising:
    a frame movable between a radially compressed configuration and a radially expanded configuration, and
    at least one expansion and locking assembly, comprising:
      an outer member, coupled to the frame at a first location, and comprising a spring biased arm with a pawl; and
      an inner member, coupled to the frame at a second location spaced apart from the first location, the inner member extending at least partially into the outer member, the inner member comprising a plurality of ratcheting teeth;
  a delivery apparatus comprising:
    a handle;
    a delivery shaft extending distally from the handle; and
    at least one actuation assembly, comprising:
      an actuator extending from the handle through the delivery shaft, and releasably coupled to the corresponding inner member; and
      a sleeve disposed around the corresponding actuator, at least one sound sensor configured to generate signals commensurate with click sounds generated during movement of the pawl over the ratcheting teeth;
  wherein the spring biased arm is biased toward the inner member; and
  wherein engagement of the pawl with the ratcheting teeth allows movement in a first direction to allow axial foreshortening and radial expansion of the frame and prevents movement in a second direction to prevent radial compression of the frame.

2. The prosthetic valve expansion monitoring system of claim 1, further comprising a control unit configured to: receive the signals from the at least one sound sensor; responsive to the received signals, determine the number of click sounds generated during the movement of the pawl; evaluate an expanded diameter of the prosthetic valve; and output an indication of the evaluated expanded diameter.

3. The prosthetic valve expansion monitoring system of claim 2, wherein the control unit is further configured to estimate the axial foreshortening of the frame by multiplying the number of click sounds by the length of a single ratcheting tooth, the evaluation of the expanded diameter being responsive to the estimated axial foreshortening.

4. The prosthetic valve expansion monitoring system of claim 3, wherein the evaluation of the expanded diameter is based on pre-stored relationships between axial foreshortening and radial expansion of the frame.

5. The prosthetic valve expansion monitoring system of claim 2, wherein the prosthetic valve comprises three expansion and locking assemblies, and wherein the control unit is further configured to differentiate between click sounds of different expansion and locking assemblies based on identification of the time difference between such click sounds.

6. The prosthetic valve expansion monitoring system of claim 1, wherein the sound sensor is disposed between the actuator and the sleeve.

7. The prosthetic valve expansion monitoring system of claim 6, wherein the sound sensor is attached to the actuator.

8. The prosthetic valve expansion monitoring system of claim 6, wherein the difference between an inner diameter of the sleeve and an outer diameter of the actuator is at least twice as large as the thickness of the sound sensor.

9. The prosthetic valve expansion monitoring system of claim 6, wherein the sleeve has a non-uniform inner diameter such that the difference between the inner diameter of the sleeve and an outer diameter of the actuator is at least twice as large as the thickness of the sound sensor at the region at which the sound sensor is positioned, and wherein the sleeve comprises a neck portion tapering distally inward to a narrower inner diameter of the sleeve.

10. A delivery assembly, comprising:
  a prosthetic valve comprising:
    a frame movable between a radially compressed configuration and a radially expanded configuration, and
    at least one expansion and locking assembly, comprising:
      an outer member, coupled to the frame at a first location, and comprising a spring biased arm with a pawl; and
      an inner member, coupled to the frame at a second location spaced apart from the first location, the inner member extending at least partially into the outer member, the inner member comprising a plurality of ratcheting teeth;
  a delivery apparatus comprising:
    a handle;
    a delivery shaft extending distally from the handle; and at least one actuation assembly, comprising:

an actuator extending from the handle through the delivery shaft, and releasably coupled to the corresponding inner member; and a sleeve disposed around the corresponding actuator, at least one vibration sensor attached to the at least one actuation assembly;

wherein the spring biased arm is biased toward the inner member;

wherein engagement of the pawl with the ratcheting teeth allows movement in a first direction to allow axial foreshortening and radial expansion of the frame and prevents movement in a second direction to prevent radial compression of the frame; and wherein the vibration sensor is configured to generate signals commensurate with vibrations generated by the expansion and locking assembly during movement of the pawl over each ratcheting tooth.

11. The delivery assembly of claim 10, further comprising a control unit configured to: receive the signals from the at least one vibration sensor; responsive to the received signals, count the vibrations generated by the expansion and locking assembly during movement of the pawl over each ratcheting tooth; responsive to an outcome of the count of the vibrations, evaluate an expanded diameter of the prosthetic valve; and output an indication of the expanded diameter.

12. The delivery assembly of claim 11, wherein the control unit is further configured to estimate the axial foreshortening of the frame by multiplying the number of vibrations generated by the expansion and locking assembly during movement of the pawl over each ratcheting tooth, by the length of a single ratcheting tooth, the evaluation of the expanded diameter responsive to the estimated axial foreshortening.

13. The delivery assembly of claim 12, wherein the evaluation of the expanded diameter of the prosthetic valve is based on pre-stored relationships between axial foreshortening and radial expansion of the frame.

14. The delivery assembly of claim 11, wherein the at least one expansion and locking assembly comprises three expansion and locking assemblies, and wherein the actuation assembly comprises three actuation assemblies, each vibration sensor attached to a separate actuation assembly coupled to corresponding expansion and locking assembly, and wherein the control unit is further configured to identify signals acquired within a predefined time period and mathematically manipulate such signals.

15. The delivery assembly of claim 14, wherein the mathematical manipulation comprises averaging the signals received within the predefined time period.

16. The delivery assembly of claim 14, wherein the control unit is further configured to identify a non-uniform expansion of the prosthetic valve, the evaluation of the expanded diameter responsive to the identified non-uniform expansion.

17. The delivery assembly of claim 16, wherein the identification of a non-uniform expansion comprises estimating the extent of axial foreshortening at more than two regions around the circumference of the prosthetic valve.

18. The delivery assembly of claim 17, wherein the identification of a non-uniform expansion comprises estimating the circumferential contour of the expanded prosthetic valve.

19. The delivery assembly of claim 10, wherein the vibration sensor is disposed between the actuator and the sleeve, and/or attached to the actuator, and wherein the difference between an inner diameter of the sleeve and an outer diameter of the actuator is at least twice as large as the thickness of the vibration sensor.

20. The delivery assembly of claim 10, wherein the vibration sensor is disposed between the actuator and the sleeve, and/or attached to the actuator, and wherein the sleeve has a non-uniform inner diameter such that the difference between the inner diameter of the sleeve and an outer diameter of the actuator is at least twice as large as the thickness of the vibration sensor at the region at which the vibration sensor is positioned, and wherein the sleeve comprises a neck portion tapering distally inward to a narrower inner diameter of the sleeve.

* * * * *